(12) United States Patent
Floratos et al.

(10) Patent No.: US 6,571,199 B1
(45) Date of Patent: May 27, 2003

(54) METHOD AND APPARATUS FOR PERFORMING PATTERN DICTIONARY FORMATION FOR USE IN SEQUENCE HOMOLOGY DETECTION

(75) Inventors: Aris Floratos, Astoria, NY (US); Isidore Rigoutsos, Astoria, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/582,045

(22) Filed: Jun. 21, 2000

Related U.S. Application Data

(60) Provisional application No. 60/106,295, filed on Oct. 30, 1998.

(51) Int. Cl.[7] ............................................. G06F 101/14
(52) U.S. Cl. .................................... 702/179; 930/310
(58) Field of Search ............................... 702/179, 180, 702/182; 930/10, 20, 30, 290, 300, 310

(56) References Cited

U.S. PATENT DOCUMENTS

| | | |
|---|---|---|
| 5,977,890 A | 11/1999 | Rigoutsos et al. |
| 6,092,065 A | 7/2000 | Floratos et al. |
| 6,108,666 A | 8/2000 | Floratos et al. |
| 6,373,971 B1 | 4/2002 | Floratos et al. |

FOREIGN PATENT DOCUMENTS

| | | |
|---|---|---|
| WO | WO 98/20433 | 5/1998 |

OTHER PUBLICATIONS

I. Rigoutsos et al., "Motif Discovery Without Alignment or Enumeration," RECOMB, New York, pp. 221–227, 1998.
A. Bairoch et al., "The PROSITE Database, it's Status in 1995," Nucleic Acids Research, vol. 24, No. 1, Oxford University Press, pp. 189–196, 1996.

M. Suyama et al., "Searching for Common Sequence Patterns Among Distantly Related Proteins," Protein Engineering, vol. 8, No. 11, Oxford University Press, pp. 1075–1080, 1995.
S.E. Stolov, "Internet: A Computer Support Tool for Building the Human Genome," Stolov Associates, Woodbury, NY, pp. 441–452, published Jun. 21, 1995.
S.F. Altschul et al., "Issues in Searching Molecular Sequence Databases," Nature Genetics, vol. 6, Review, pp. 119–129, Feb. 1994.
A.F. Neuwald et al., "Detecting Patterns in Protein Sequences," J. Mol. Biol. 239, Academic Press Limited, pp. 698–712, 1994.
Part II, Sequence Analysis, Chapter 9, Pattern Discovery, pp. 130–169, Sep. 1993.
A. Califano et al., "FLASH: A Fast Look–Up Algorithm for String Homology," Proceedings 1993 IEEE Computer Society Conference on Computer Vision and Pattern Recognition, NY, pp. 353–359, Jun. 15–18, 1993.

(List continued on next page.)

*Primary Examiner*—Marc S. Hoff
*Assistant Examiner*—Edward Raymond
(74) *Attorney, Agent, or Firm*—Ryan, Mason & Lewis, LLP; Casey P. August

(57) ABSTRACT

In a dictionary formation aspect of the invention, a computer-based method of processing a plurality of sequences in a database comprises the following steps. First, the method includes evaluating each of the plurality of sequences including characters which form each sequence. Then, at least one pattern of characters is generated representing at least a subset of the sequences in the database. The pattern has a statistical significance associated therewith, the statistical significance of the pattern being determined by a value representing a minimum number of sequences that the pattern supports in the database.

21 Claims, 20 Drawing Sheets

OTHER PUBLICATIONS

S. Henikoff et al., "Amino Acid Substitution Matrices from Protein Blocks," Proc. Natl. Acad. Sci. USA, vol. 89, pp. 10915–10919, Nov. 1992.

S. Henikoff et al., "Automated Assembly of Protein Blocks for Database Searching," Nucleic Acids Research, vol. 19, No. 23, Oxford University Press, pp. 6565–6572, 1991.

S. Karlin et al., "Methods for Assessing the Statistical Significance of Molecular Sequence Features by Using General Scoring Schemes," Proc. Natl. Acad. Sci. USA, vol. 87, pp. 2264–2268, Mar. 1990.

S.F. Altschul et al., "Basic Local Alignment Search Tool," J. Mol. Biol. 215, pp. 403–410, Academic Press Limited, 1990.

W.R. Pearson et al., "Improved Tools for Biological Sequence Comparison," Proc. Natl. Acad. Sci. USA, vol. 85, pp. 2444–2448, Apr. 1988.

A.F.W. Coulson et al., "Protein and Nucleic Acid Sequence Database Searching: a Suitable Case for Parallel Processing," The Computer Journal, vol. 30, No. 5, pp. 420–424, 1987.

D.J. Lipman et al., "Rapid and Sensitive Protein Similarity Searches," Science, vol. 227, No. 4693, pp. 1435–1441, Mar. 22, 1985.

T.F. Smith et al., "Identification of Common Molecular Subsequences," J. Mol. Biol. 147, pp. 195–197, Academic Press Inc. (London) Ltd., 1981.

S.B. Needleman et al., "A General Method Applicable to the Search for Similarities in the Amino Acid Sequence of Two Proteins," J. Mol. Biol. 48, pp. 443–453, 1970.

Rigoutsos et al., "Combinational Pattern Discovery in Biological Sequences: the TEIRESIAS Algorithm," Bioinformatics, vol. 14, No. 1, 55–67 (1998).

Yamaguchi et al., "Protein Motif Discovery from Amino Acid Sequence by Sets of Regular Patterns, " Research Report of Information Processing Society, Information Processing Society, vol. 95, No. 76, 33–40, (Jul. 28, 1995).

| Q = AFGHIKLPNMKAMGH | | |
|---|---|---|
| W = 4, POSITION = 6 | | |
| SUBSTRING STARTING AT POSITION 6 | | HASH VALUE |
| KL | (first_char = K, last_char = L, gap = 0) | 1,184 |
| KLP | (first_char = K, last_char = P, gap = 1) | 1,601 |
| KLPN | (first_char = K, last_char = N, gap = 2) | 1,394 |
| KLPNM | (first_char = K, last_char = M, gap = 3) | 1,291 |

▧ REGIONS IN Q AND Sj MATCHING A PATTERN P; (i,j,k,l) THE CORRESPONDING SEGMENT
☐ REGIONS IN Q AND Sj MATCHING A PATTERN P'; (i',j,k',l') THE CORRESPONDING SEGMENT
▨ THE RESULT OF CHAINING TOGETHER THE ABOVE TWO SEGMENTS

```
GIVEN A DATABASE D, FORM REDUNDANT
GROUPS BY IDENTIFYING AND GROUPING          — 1602
TOGETHER HIGHLY SIMILAR PROTEINS
            ↓
FORM "CLEANED-UP" DATABASE D' BY
INCLUDING THEREIN:
-SEQUENCES IN D THAT ARE NOT SUFFICIENTLY   — 1604
 HOMOLOGOUS TO OTHER PROTEINS
-LONGEST SEQUENCE FROM EACH REDUNDANT GROUP
            ↓
RUN TEIRESIAS ALGORITHM ON EACH REDUNDANT GROUP — 1606
```

FIG. 17

| NUMBER OF SEQUENCES/aa IN ORIGINAL DATABASE | NUMBER OF HIGHLY SIMILAR SEQUENCES/GROUPS | NUMBER OF SEQUENCES/aa IN CLEANED-UP DATABASE |
|---|---|---|
| 59,021/21,210,388 | 40,407/9,165 | 27,779/10,596,414 |

FIG. 18

| TOTAL NUMBER OF PATTERNS | NUMBER OF PROTEINS COVERED | NUMBER OF AMINO ACIDS COVERED | AVERAGE PERCENTAGE OF PROTEIN LENGTH COVERED |
|---|---|---|---|
| 565,432 | 57,983 | 12,567,345 | 58.1% |

FIG. 20(a)

| ATP/GTP-BINDING P-loop VARIATIONS | PROTEIN KINASE ACTIVE SITE |
|---|---|
| G..G.GKST | HRDgK..N.L |
| G..G.GKaTL | HRDhKP.N |
| G..G.GKTT | H.DiKP.N.L |
| G..G.GKS.L | HRDL...N.L |
| G..G.GKT.L | RDjKP.N.L |
| L.G..G.GKbT | I.HRDiK..N |
| L.G..G.GKT | HRDkK..NI |
| L.G..G.GK..L | I.H.DiK..N.L |
| G..GSGKS | HRDLK..N |
| GP.G.GKT | IHRD....N.L |
| G..GSGKcT | H.DL.P.N.L |
| G....GKSTL | |
| L.G..G.GKS | HOMEOBOX DNA-BINDING MOTIF |
| G..G.GKS..L | WFQN.R.K |
| L...G..G.GKT | WFmNRR.K |
| G.GKST....L | WFQNRR |
| G.SG.GKS | WFQN.R.n.K |
| I.G..G.GKS | V.oWFpNRR |
| G.GKSTL | QV.oWFqNR |
| G.GK.TL...L | |
| L.G....GKST | ABC TRANSPORTER SIGNATURE |
| G...SGKST | LSGG...R...A |
| G....GKdTLL | |
| G.GKTT....L | ATP-BINDING SITE PROTEIN KINASES |
| G..G.GKT..A | LG.G.FG.V |
| G..GSGKT | LSGG.....A.A |
| V...G..G.GKT | |
| G....GKTTL | VARIOUS ATP-BINDING/DOWNSTREAM BOX |
| I.G..G.GKT | L.LDE....LD |
| G....GKST.L | L.LDE.T..L |
| I...G..GKT | |
| G.GKTTL | COLLAGEN, VARIOUS P/G-REPEATS |
| G.GKS.L...L | G.PG..G.PG |
| G....GKS.LL | G..G.PG..G.P |
| L.G....GKT.L | G.PG..G..G.P |
| GSGKST | G..GP.GP.G |
| G..GSG.ST | G.PG.PG..G |
| I.G....GKST | PG..G.PG..G |
| V.L.G..G.GK | G...G.PG.PG |
| L.G....GKTT | GP.G..G.PG |
| I.G....GKS.L | PG.PG..G.P |
| G....GKT.LL | G.PG.PG....P |
| L.G..G.G.T.L | PG.PG....PG |
| G....GKTT.L | G..G..GAPG |
| GP...GKT.L | |

FIG. 20 (b)

| | |
|---|---|
| G.SG.G.ST | ZINC FINGER, TRANSCIPTION FACTORS |
| G..G.G.S.LL | H.R.H.GEsP |
| L.G....GKS.L | H...HTGEtP |
| G.GKT..A...A | H.R.HT.E.P |
| I.G.SG.GK | R.H.G.KP..C |
| G.GKT.....LA | |
| L.eP.G.GKT | PROTEIN KINASES |
| GP...GKT..A | GT..Y.APE |
| V.I.G..G.GK | |
| TGSGKT | NUCLEAR HORMONE RECEPTORS |
| I.G....GKTT | CRu.KC...GM |
| G...SGKS..L | C.vC..FFRR |
| G.SGSG.S | |
| G.fKSTL...L | |

FIG. 21

| | | | |
|---|---|---|---|
| H31_HUMAN (302) | H3_DROME (302) | H32_BOVIN (302) | H3_STRPU (300) | H3_PSAMI (300) |
| H32_XENLA (298) | H3_ACRFO (297) | H3_CAEEL (291) | H3_VOLCA (289) | H32_MEDSA (288) |
| H3_ENCAL (288) | H3_CHLRE (287) | H31_SCHPO (286) | H3_PEA (284) | H3_MAIZE (284) |
| H33_CAEEL (284) | H33_HUMAN (284) | H33_SCHPO (277) | H31_TETPY (274) | H34_CAIMO (272) |
| H3_EMENI (271) | H3_NEUCR (271) | H3_YEAST (269) | H32_ORYSA (269) | YB21_CAEEL (232) |
| H3_HORVU (221) | H34_MOUSE (204) | H3_ENTHI (179) | H32_TETAM (177) | H32_TETPY (176) |
| H33_TETTH (168) | H32_TETBO (153) | H3_LEIIN (110) | CENA_HUMAN (100) | CSE4_YEAST (96) |
| YL82_CAEEL (86) | CENA_BOVIN (84) | YMH3_CAEEL (79) | H3_NARPS (64) | |

FIG. 22

```
Score = 269
************************************************************
Local Alignment(s) with the sequence H3_YEAST
Query   0
        ARTKQTARKSTGGKAPRKQLATKAARKS
        ARTKQTARKSTGGKAPRKQLA+KAARKS
        ARTKQTARKSTGGKAPRKQLASKAARKS
Seq     0
------------------------------------------------------------
Query   33
        GVKKPHRYRPGTVALREIRRYQKSTELLIRKLPFQRLVREIAQDFKTDLRFQ
        GVKKPHRY+PGTVALREIRR+QKSTELLIRKLPFQRLVREIAQDFKTDLRFQ
        GVKKPHRYKPGTVALREIRRFQKSTELLIRKLPFQRLVREIAQDFKTDLRFQ
Seq     33
------------------------------------------------------------
Query   96
        EAYLVGLFEDTNLCAIHAKRVTIMPKDIQLARRIRGERA
        EAYLV LFEDTNL AIHAKRVTI  KDI LARR+RGER
        EAYLVSLFEDTNLAAIHAKRVTIQKKDIKLARRLRGERS
Seq     96
------------------------------------------------------------

Score = 100
************************************************************
Local Alignment(s) with the sequence CENA_HUMAN
Query   45
        VALREIRRYQKSTELLIRKLPFQRLVR
          L+EIR+ QKST LLIRKLPF RL R
        GWLKEIRKLQKSTHLLIRKLPFSRLAR
Seq     45
------------------------------------------------------------
Query   77
        FKTDLRFQSSAVMALQEACEAYLVGLFEDTNLCAIHAK
            D  Q  A++ALQEA EA+LV LFED  L  +HA
        RGVDFNWQAQALLALQEAAEAFLVHLFEDAYLLTLHAG
Seq     79
------------------------------------------------------------
Query   111
        IHAKRVTIMPKDIQLARRIRGERA
        +HA RVT +PKD+QLARRIRG
        LHAGRVTLFPKDVQLARRIRGLEE
Seq     113
------------------------------------------------------------
```

FIG. 23

```
Score = 51
*************************************************************
Local Alignment(s) with the sequence NTNO_HUMAN Query       196
            VEKDILPHKVAFTGGGLRFILYPERPILEE
            E  +    VA G+GL FILYPE
            HEHKVNIEDVATEGAGLVFILYPEAISTLS
Seq         369
----------------------------------------------------------

Score = 51
*************************************************************
Local Alignment(s) with the sequence NTNO_BOVIN Query       196
            VEKDILPHKVAFTGGGLRFILYPERPILEE
            E  +    VA G+GL FILYPE
            HEHKVNIEDVATEGAGLVFILYPEAISTLS
Seq         367
----------------------------------------------------------

Score = 49
*************************************************************
Local Alignment(s) with the sequence KAPL_APLCA Query       816
            NAMIEMFKENYKLLKEYLETDIEVLKELDKNYK
            A   +F E  K LKEYLE+ +E     L
            MAHNQVFPESQKWLKEYLESSLEQFENLFNKNV
Seq         0
----------------------------------------------------------
```

FIG. 24

```
Local alignments of sequence ----> YZ28_METJA along the pattern Y..S..I...DLK Local alignment with the sequence ---> MP38_MOUSE
Score = 27
Query    24
         DKYQINVSGIYNISDDILESDLKLHIAQLLFLI
            YQI     Y S DI+  DLK      +
         LIYQILRGLKYIHSADIIHRDLKPSNLAVNEDC
Seq     129
_____

Local alignment with the sequence ---> MKK2_DROME
Score = 22
Query    24
         DKYQINVSGIYNISDDILESDLKLHIAQLLFLI
              I     Y S DI   DLK
         IMHEICAAVDYLHSRDIAHRDLKPENLLYTTTQ
Seq     121
_____

Local alignment with the sequence ---> MP38_XENLA
Score = 22
Query    24
         DKYQINVSGIYNISDDILESDLKLHIAQLLFLI
            YQI     Y S I+   DLK      +
         LIYQILRGLKYIHSAGIIHRDLKPSNLAVNEDC
Seq     130
_____

Local alignment with the sequence ---> KRAF_CAEEL
Score = 20
Query    24
         DKYQINVSGIYNISDDILESDLKLHIAQLLFLI
             Q+ +   Y S I+   DLK   L+  +
         ILKQVSLGMNYLHSKNIIHRDLKTNNIFLMDDM
Seq     581
_____
```

FIG. 25

| MP38_MOUSE | MKK2_DROME | MP38_XENLA | KRAF_CAEEL | DAPK_HUMAN |
|---|---|---|---|---|
| PKX1_HUMAN | KAPC_YEAST | KAPA_YEAST | ASK2_ARATH | KCC1_YEAST |
| CC28_YEAST | KD82_SCHPO | SPK1_YEAST | SGK_RAT | GCN2_YEAST |
| FUSE_DROME | NABA_RAT | KAPC_ASCSU | KKK1_YEAST | KGPA_BOVIN |
| KGPB_HUMAN | KGP3_DROME | KGP2_DROME | KDC2_DROME | |

FIG. 26

| CC7_SCHPO | CDK2_ENTHI | CDK6_HUMAN | IPL1_YEAST | JKK1_HUMAN |
|---|---|---|---|---|
| JKK1_MOUSE | KG1Z_YEAST | KKIA_HUMAN | KNQ1_YEAST | KPBG_MOUSE |
| KPBG_RABIT | KPBG_RAT | KS61_MOUSE | KS62_HUMAN | KS62_MOUSE |
| KS6A_CHICK | KS6A_XENLA | KS6B_XENLA | MKK2_YEAST | MPK1_HUMAN |
| MPK1_MOUSE | MPK1_RABIT | MPK1_RAT | MPK1_XENLA | MPK2_HUMAN |
| MPK2_RAT | MPK2_XENLA | PAK1_SCHPO | PK3_DICDI | PKD1_DICDI |
| PKX1_HUMAN | ST20_YEAST | YFH8_YEAST | YLI1_MYCHO | |

FIG. 27

| ASK1_ARATH | ASK2_ARATH | CC2C_DROME | CC2_DICDI | CC2_SCHPO |
|---|---|---|---|---|
| CDK7_CARAU | CDK7_HUMAN | CDK7_MOUSE | CDK7_RAT | CDK7_XENLA |
| CTR1_ARATH | FUSE_DROME | GCN2_YEAST | KCC4_YEAST | KD82_SCHPO |
| KEMK_MOUSE | KFD3_YEAST | KKK1_YEAST | KP78_HUMAN | KPBG_MOUSE |
| KPBG_RABIT | KPBG_RAT | KPBH_HUMAN | KPBH_RAT | KPK1_ARATH |
| KPSC_HUMAN | SNF1_CANAL | SNF1_YEAST | SRK6_BRAOL | YNA3_CAEEL |

FIG. 29

```
####################################################################
ID   ASK1_ARATH    STANDARD;   PRT;      363 AA.
DE   SERINE/THREONINE-PROTEIN KINASE ASK2 (EC 2.7.1.-).
-------> I.H.DLK.......D: Matching at offset 119
FT   DOMAIN           4     260        PROTEIN KINASE.
FT   ACT_SITE       123     123        BY SIMILARITY.
####################################################################
ID   ASK2_ARATH    STANDARD;   PRT;      353 AA.
DE   SERINE/THREONINE-PROTEIN KINASE ASK2 (EC 2.7.1.-).
-------> I.H.DLK......D: Matching at offset 119
FT   DOMAIN           4     260        PROTEIN KINASE.
FT   ACT_SITE       123     123        BY SIMILARITY.
####################################################################
ID   CC2C_DROME    STANDARD;   PRT;      314 AA.
DE   CELL DIVISION CONTROL PROTEIN 2 COGNATE (EC 2.7.1.-).
-------> I.H.DLK......D: Matching at offset 126
FT   DOMAIN           8     287        PROTEIN KINASE.
FT   ACT_SITE       130     130        BY SIMILARITY.
####################################################################
ID   CC2_DICDI     STANDARD;   PRT;      296 AA.
DE   CELL DIVISION CONTROL PROTEIN 2 HOMOLOG(EC 2.7.1.-)(P34 PROTEIN
DE   KINASE).
-------> I.H.DLK.......D: Matching at offset 125
FT   DOMAIN          10     288        PROTEIN KINASE.
FT   ACT_SITE       129     129        BY SIMILARITY.
####################################################################
ID   CC2_SCHPO     STANDARD;   PRT;      297 AA.
DE   CELL DIVISION CONTROL PROTEIN 2(EC 2.7.1.-)(P34 PROTEIN KINASE).
-------> I.H.DLK......D: Matching at offset 130
FT   DOMAIN           4     293        PROTEIN KINASE.
FT   ACT_SITE       134     134        BY SIMILARITY.
```

METHOD AND APPARATUS FOR PERFORMING PATTERN DICTIONARY FORMATION FOR USE IN SEQUENCE HOMOLOGY DETECTION

CROSS-REFERENCE TO RELATED APPLICATIONS

The present application claims priority to provisional U.S. patent application No. 60/106,295, filed Oct. 30, 1998, in the names of A. Floratos and I. Rigoutsos, and is related to U.S. patent application, entitled "Methods and Apparatus for Performing Sequence Homology Detection," filed concurrently herewith, in the names of A. Floratos and I. Rigoutsos, the disclosures of which are incorporated herein by reference.

FIELD OF THE INVENTION

The present invention relates generally to database searches and, more particularly, to methods and apparatus for detecting sequence homology between a query sequence and sequences in a database in association with a given application, e.g., genetic research.

BACKGROUND OF THE INVENTION

In the area of genetic research, the first step following the sequencing of a new gene is an effort to identify that gene's function. The most popular and straightforward methods to achieve that goal exploit the following biological fact—if two peptide stretches exhibit sufficient similarity at the sequence level (i.e., one can be obtained from the other by a small number of insertions, deletions and/or amino acid mutations), then they probably are biologically related. Examples of such an approach are described in A. M. Lesk, "Computational Molecular Biology," Encyclopedia of Computer Science and Technology; A. Kent and J. G. Williams editors, 31:101–165, Marcel Dekker, New York, 1994; R. F. Doolittle, "What we have learned and will learn from sequence databases," Computers and DNA, G. Bell and T. Marr editors, 21–31, Addison-Wesley, 1990; C. Caskey, R. Eisenberg, E. Lander, and J. Straus, "Hugo statement on patenting of DNA," Genome Digest, 2:6–9, 1995; and W. R. Pearson, "Protein sequence comparison and protein evolution," Tutorial of Intelligent Systems in Molecular Biology, Cambridge, England, 1995.

Within this framework, the question of getting clues about the function of a new gene becomes one of identifying homologies in strings of amino acids. Generally, a homology refers to a similarity, likeness, or relation between two or more sequences or strings. Thus, one is given a query sequence Q (e.g., the new gene) and a set D of well characterized proteins and is looking for all regions of Q which are similar to regions of sequences in D.

The first approaches used for realizing this task were based on a technique known as dynamic programming. This approach is described in S. B. Needleman and C. D. Wunsch, "A General Method Applicable To The Search For Similarities In The Amino Acid Sequence Of Two Proteins," Journal Of Molecular Biology, 48:443–453, 1970; and T. F. Smith and M. S. Waterman, "Identification Of Common Molecular Subsequences," Journal Of Molecular Biology, 147:195–197, 1981. Unfortunately, the computational requirements of this method quickly render it impractical, especially when searching large databases, as is the norm today. Generally, the problem is that dynamic programming variants spend a good part of their time computing homologies which eventually turn out to be unimportant.

In an effort to work around this issue, a number of algorithms have been proposed which focus on discovering only extensive local similarities. The most well known among these algorithms are referred to as FASTA and BLAST. The FASTA algorithm is described in W. R. Pearson, and D. J. Lipman, "Improved tools for biological sequence comparison," Proc. Natl. Acad. Sci., 85:2444–2448, 1988; and D. J. Lipman, and W. R. Pearson, "Rapid and sensitive protein similarity searches," Science, 227:1435–1441, 1989. The BLAST algorithm is described in S. Altschul, W. Gish, W. Miller, E. W. Myers, and D. Lipman, "A basic local alignment search tool," J. Mol. Biology, 215:403–410, 1990. In the majority of the cases, increased performance is achieved by first looking for ungapped homologies, i.e., similarities due exclusively to mutations and not insertions or deletions. The rationale behind this approach is that in any substantial gapped homology between two peptide strings, chances are that there exists at least a pair of substrings whose match contains no gaps. The locating of these substrings (the ungapped homology) can then be used as the first step towards obtaining the entire (gapped) homology.

Identifying the similar regions between the query and the database sequences is, however, only the first part (the computationally most demanding) of the process. The second part (the one that is of interest to biologists) is evaluating these similarities, i.e., deciding if they are substantial enough to sustain the inferred relation (functional, structural or otherwise) between the query and the corresponding data base sequence(s). Such evaluations are usually performed by combining biological information and statistical reasoning. Typically, similarity is quantified as a score computed for every pair of related regions. Computation of this score involves the use of gap costs (for gapped alignments) and of appropriate mutation matrices giving the evolutionary probability of any given amino acid changing into another. Examples of these matrices are the PAM matrix (see M. O. Dayhoff, R. M. Schwartz and B. C. Orcutt, "A model of evolutionary change in proteins," Atlas of Protein Sequence and Structure, 5:345–352, 1978) and the BLOSUM matrix (see S. Henikoff and J. G. Henikoff, "Amino acid substitution matrices from protein blocks," Proc. Natl. Acad. Sci., 89:915–919, 1992). Then, the statistical importance of this cost is evaluated by computing the probability (under some statistical model) that such a score could arise purely by chance, e.g., see S. Karlin, A. Dembo and T. Kawabata, "Statistical composition of high-scoring segments from molecular sequences," The Annals of Statistics, 2:571–5 81, 1990; and S. Karlin and S. Altschul, "Methods for assessing the statistical significance of molecular sequence features by using general scoring schemes," Proc. Natl. Acad. Sci., 87:2264–2268, 1990. Depending on the statistical model used, this probability can depend on a number of factors such as: the length of the query sequence, the size of the underlying database, etc. No matter, however, what conventional statistical model one uses there are always the so called "gray areas," i.e., situations where a statistically unimportant score indicates really a biologically important similarity. Unfortunate as this might be, it is also inescapable; there is after all a limit to how well a statistical model can approximate the biological reality.

An alternative to the inherent difficulty of attaching statistical importance to weak similarities is the use of biological knowledge in deducing sequence descriptors that model evolutionary distant homologies. BLOCKS (see S. Henikoff and J. Henikoff, "Automatic Assembly of Protein Blocks for Database Searching," Nucleic Acids Research, 19:6565–6572, 1991) is a system that employs pattern-induced profiles obtained over the protein classification defined in the PROSITE (see S. Henikoff and J. Henikoff, "Protein Family Classification Based on Searching a Database of Blocks," Genomics, Vol. 19, pp. 97–107, 1994) database in order to functionally annotate new genes. The advantage here is that this classification is compiled by experts working with families of proteins known to be related. As a result, even weak similarities can be recognized and used in the annotation process. On the other hand, there is only that much knowledge about which proteins are indeed related and consequently being representable by a pattern. Furthermore, there is always the danger that a family of proteins actually contains more members than is currently thought of. By excluding these other members from consideration, it is possible to get patterns that "over fit" the family, i.e., they are too strict to extrapolate to the unidentified family members.

Therefore, it is evident that there exists a need for methods and apparatus for creating improved pattern dictionaries through unique dictionary formation techniques that permit improved sequence homology detection, as well as a need for methods and apparatus for sequence homology detection, itself, which are not limited to searching only annotated sequences.

SUMMARY OF THE INVENTION

The present invention provides solutions to the above and other needs by providing improved pattern dictionary formation techniques and improved sequence homology detection techniques, as will be described in greater detail below.

In a sequence homology detection aspect of the invention, a computer-based method of detecting homologies between a plurality of sequences in a database and a query sequence comprises the following steps. First, the method includes accessing patterns associated with the database, each pattern representing at least a portion of one or more sequences in the database. Next, the query sequence is compared to the patterns to detect whether one or more portions of the query sequence are homologous to portions of the sequences of the database represented by the patterns. Then, a score is generated for each sequence detected to be homologous to the query sequence, wherein the sequence score is based on individual scores generated in accordance with each homologous portion of the sequence detected, and the sequence score represents a degree of homology between the query sequence and the detected sequence.

In a dictionary formation aspect of the invention, a computer-based method of processing a plurality of sequences in a database comprises the following steps. First, the method includes evaluating each of the plurality of sequences including characters which form each sequence. Then, at least one pattern of characters is generated representing at least a subset of the sequences in the database. The pattern has a statistical significance associated therewith, the statistical significance of the pattern being determined by a value representing a minimum number of sequences that the pattern supports in the database.

Accordingly, in a significant departure from prior art approaches, the methodologies of the invention are based on the unsupervised pattern discovery performed on arbitrary data bases without requiring any prior partition of the database. The BLOCKS approach assumes that the database has been partitioned (by outside experts) in subsets of biologically related sequences. Profiles are then obtained by individually processing each subset. As a result of this approach, BLOCKS cannot handle arbitrary databases, since not all such databases are partitioned in related subsets. In fact, BLOCKS works only with the SwissProt database, referenced herein, using the protein groups described in the PROSITE database, also referenced herein. The present invention, on the other hand, preferably uses the entire database as its input and provides for an automated methodology to decide which patterns are important and which are not.

Further, the present invention provides a new statistical framework for evaluating the statistical importance of the discovered patterns. Unlike existing frameworks, the approach of the invention introduces the concept of memory in its computations. That is, for example, when a region A on the query sequence is compared with a region B on some database sequence, the resulting similarity score is evaluated by taking into account the similarity of A to all the other sequences in the database.

The use of the enhanced statistical model described herein allows the detection of important local similarities which, using existing approaches, would go undetected. This allows the system of the invention to perform similarity searches at a higher level of sensitivity than is possible using prior art systems.

Still further, the present invention provides an automated method to utilize partial annotation information available in the underlying database D. This methodology allows the user to exploit in greater detail similarities that seem unimportant. For example, when a pattern matches the query sequence region A, all the database regions also matching that pattern can be inspected. If all (or more) of these database regions are annotated in the same way, then this annotation can be transferred to the query region A. Partially annotating the query sequence in the above manner can prove useful towards the overall sequence annotation.

The present invention also provides for a detailed methodology to cluster the database into groups of highly homologous sequence. In a genetic data processing application, this methodology allows for the correct treatment of multi-domain proteins.

It is also to be appreciated that the inventive concepts described herein may be implemented on a network such as, for example, the Internet, in a client-server relationship. This allows a user to enter a query sequence at a client device at a remote location that is transmitted to a server over the network and processed at the server. The server then returns the results of the homology search to the client device of the user via the network.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 16 is a flow diagram illustrating a database clean up process according to one embodiment of the present invention; and FIGS. 17 through 30 are diagrams illustrating experimental results associated with the present invention.

DETAILED DESCRIPTION OF PREFERRED EMBODIMENTS

The present invention will be explained below in the context of an illustrative genetic data processing application. However, it is to be understood that the present invention is not limited to such a particular application. Rather, the invention is more generally applicable to creating pattern dictionaries from arbitrary databases (after appropriately translating database records to an equivalent sequence representation) and performing unrestricted homology searches of any given query record against the data in the database.

Figure 1:
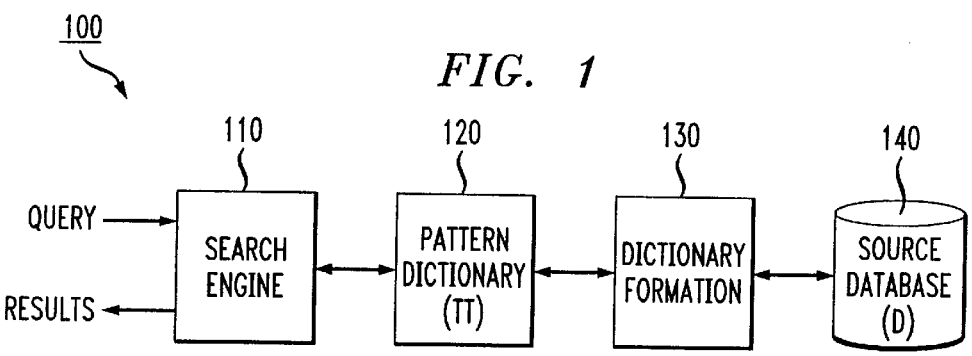
FIG. 1 is a block diagram of a sequence homology detection system according to an embodiment of the present invention.

Referring initially to FIG. 1, a block diagram of a sequence homology detection system according to an embodiment of the present invention is shown. The illustrative system 100 includes a search engine module 110, a pattern dictionary 120, a dictionary formation module 130 and a source database 140. As will be explained in detail below, the search engine 110 receives a query sequence from a user and performs a search of the pattern dictionary 120 to attempt to locate patterns stored in the dictionary which represent sequences from the database 140 that are similar in some way to the query sequence. Prior to a query, the dictionary formation module 130 creates the pattern dictionary 120 from the database 140. This dictionary formation process is referred to as information gathering or mining. The search engine 110 returns some or all of the query results (e.g., homologous sequences from the database) to the user.

Figure 2:
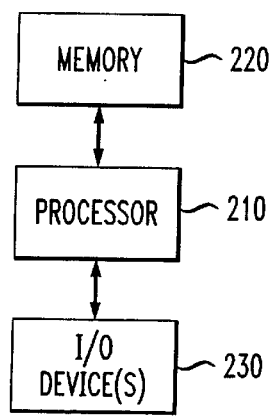
FIG. 2 is a block diagram of an exemplary hardware implementation of a sequence homology detection system of the present invention.

FIG. 2 is a block diagram of an exemplary hardware implementation of the sequence homology detection system 100. As shown, the system 100 may be implemented in accordance with a processor 210, a memory 220 and I/O devices 230. It is to be appreciated that the term "processor" as used herein is intended to include any processing device, such as, for example, one that includes a CPU (central processing unit). The term "memory" as used herein is intended to include memory associated with a processor or CPU, such as, for example, RAM, ROM, a. fixed memory device (e.g., hard drive), a removable memory device (e.g., diskette), flash memory, etc. In addition, the term "input/output devices" or "I/O devices" as used herein is intended to include, for example, one or more input devices, e.g., keyboard, for making queries and/or inputting data to the processing unit, and/or one or more output devices, e.g., CRT display and/or printer, for presenting query results and/or other results associated with the processing unit. It is also to be understood that the term "processor" may refer to more than one processing device and that various elements associated with a processing device may be shared by other processing devices. Accordingly, software components including instructions or code for performing the methodologies of the invention, as described herein, may be stored in one or more of the associated memory devices (e.g., ROM, fixed or removable memory) and, when ready to be utilized, loaded in part or in whole (e.g., into RAM) and executed by a CPU.

Figure 3:
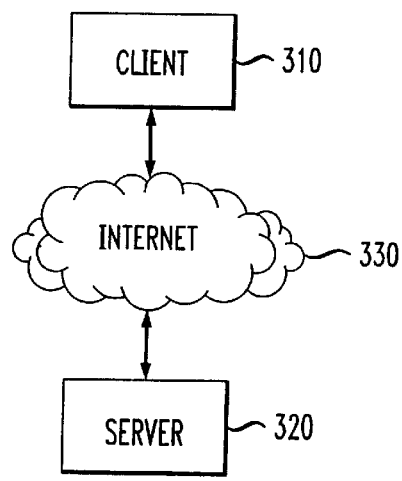
FIG. 3 is a block diagram of a network-based implementation of a sequence homology detection system of the present invention.

FIG. 3 is a block diagram of a network-based implementation of the sequence homology detection system of the present invention. As shown, a client computer system 310 is in communication with a server computer system 320 via a network 330 such as, for example, the Internet. However, the network could also be a private network and/or a local network. According to the implementation of FIG. 3, all or a portion of the elements of system 100 shown in FIG. 1 reside on and are executed by the server 330. A user operating remotely on his client computer system, e.g., a personal computer, laptop and/or some other type of personal processing device, enters a query sequence through application software running on the computer system, e.g., web browsing software and/or a graphical user interface associated with the search engine. The query is passed over the network 330, in a conventional manner, and processed by server 320. The server 320 receives the query and executes the search engine methodologies of the invention in accordance with a stored pattern dictionary. The dictionary may have been formed by a dictionary formation module of the invention in accordance with a source database. The server returns some or all of the query results (e.g., homologous sequences from the database) to the client via the network. It is to be understood that the server may represent more than one computer system. That is, one or more of the elements in FIG. 1 may reside on and be executed by their own computer system, e.g., with its own processor, memory and I/O devices.

Given a general description of the elements of the sequence homology detection system of the invention and various exemplary hardware implementations, the various inventive methodologies will now be explained in detail.

The respective methodologies associated with the search engine module 110 and the dictionary formation module 130 will be described below together in an illustrative embodiment associated with the sequence homology detection system 100. However, it is to be understood that the inventive methodology associated with the search engine module may be utilized with other known pattern dictionaries. Likewise, the inventive methodology associated with the dictionary formation module may be employed to create pattern dictionaries for use with other known search engines.

For ease of reference, the remainder of detailed description will be divided into sections as follows: (I) Definitions;

(II) Search Engine; (III) Dictionary Formation; and (IV) Experimental Results.

I. Definitions

The following section provides some notation that is used below to describe various aspects of the invention.

Σ refers to the set of characters used for constructing sequences. In the biological setting (the one preferably addressed here), the sequences that we are dealing with are proteins and the set Σ is the set of the 20 amino acids. The terms protein/sequence will be used interchangeably below, and the same is true for the terms character/amino acid.

D refers to the underlying database of proteins, the one that the collection of patterns (pattern dictionary or bio-dictionary) is built upon. An example database that we will be using throughout this description is the following (containing three sequences)

D={$s_1$, $s_2$, $s_3$}, where $s_1$=ARQSTLUMNPQ $s_2$=FDSALQFTGMRA $s_3$=RKMFPQDDSLA Π refers to a collection of patterns, i.e., referred to herein as the bio-dictionary or the pattern dictionary 120. The exact method of obtaining Π will be explained below in the section entitled "Dictionary Formation." Patterns are regular expressions describing families of peptides. The polypeptide family represented by a single pattern is expected to contain stretches of related (structurally, functionally, evolutionary) amino acids. More specifically, given the alphabet Σ of amino acids, we define a pattern P in Π as a regular expression of the form:

$$\Sigma(\Sigma \cup \{\text{'.'}\})^*\Sigma,$$

where '.' (Referred to as the "don't care character") denotes a position that can be occupied by an arbitrary residue. Being a regular expression, every pattern P defines a language of polypeptides consisting of all strings that can be obtained from P by substituting each don't care character by an arbitrary residue from Σ. Also, each P in Π matches at least $K_{min}$ sequences in D. $K_{min}$ is an integer and its computation is explained below in the "Dictionary Formation" section. In the example below, we will assume a specified value. The regions of the database sequences matching a pattern P are recorded in an offset list $L_D(P)$ of the pattern P. This is a list containing all the pairs (j, k) such that the pattern P matches the j-th sequence of the database at offset k.

For the example database introduced above, and assuming that $K_{min}$=2, the set of patterns is P={A.Q.T, M.PQ}. The two patterns in this set appear in the following input sequences (the matching positions are shown in bold-case):

| A.Q.T | M.PQ |
|---|---|
| $s_1$: ARQSTLUMNPQ | $s_1$: ARQSTLUMNPQ |
| $s_2$: FDSALQFTGMRA | $s_3$: RKMFPQDDSLA |

The offset lists of the two patterns are as follows:

$L_D$(A.Q.T)={(1, 1), (2, 4)}

$L_D$(M.PQ)={(1, 8), (3, 3)}

It is to be appreciated that the first term in each parenthetical is the sequence number and the second term is the offset. The offset corresponding to any character in a sequence is the distance of that character from the beginning of the sequence. For example, (2, 4) denotes that the sequence is $s_2$ and that the pattern A.Q.T begins at a distance of four characters from the beginning of sequence $s_2$.

Q refers to the query protein. An objective of the search engine of the invention is to identify sequence homologies between the database sequences in D and any query sequence Q that the user may supply. As an example, we will use the query Q=JLANQFTLMDPQDLA. This sequence has a number of homologous regions with the database sequences. Below, we are showing some of them (again, pairs of similar regions are shown in bold-case):

| Q: JLANQFTLMDPQDLA | Q: JLANQFTLMDPQDLA |
|---|---|
| $s_1$: ARQSTLUMNPQ | $s_2$: FDSALQFTGMRA |

Thus, the search engine identifies similarities such as the ones shown above. Two regions of equal length are similar if, when put one under the other, they have several matching characters lined up together. The exact notion of similarity will be made precise in what follows; for now, it suffices to say that it involves the use of scores for every possible pair of characters. Every such score is a measure of fitness, identifying how biologically probable it is for two characters to be lined up together.

Given a pattern P, a "backbone" of P is defined as a string over the alphabet {1, 0} obtained from P by turning every residue of P into the character '1' and every don't care into the characters '0'. For example, the backbone of the pattern P="A . . . DFE" is the string "100111". Backbones partition the set of patterns into equivalent classes with each class containing all the patterns sharing the same backbone.

Another concept that may be employed in accordance with the invention is that of the "density" of a pattern. Generally, the density describes the minimum amount of homology between any two members of G(P) (where G(P) refers to the language of polypeptides consisting of all strings that can be obtained from P by substituting each don't care character by an arbitrary residue from Σ) and is defined by two integers L and W (L≦W): a pattern P has an <L, W> density if every substring of P that starts and ends with an amino acid and has length at least W contains L or more residues. In every such pattern, the ratio of the number of residues over the length of the pattern is at least L/W. The integers L and W are parameters of our preferred method and their values control the amount of similarity allowed in the searches performed. These parameters are also described in detail in a U.S. patent application identified by Ser. No. 09/023,756, filed on Feb. 13, 1998, directed toward the "TEIRESIAS" algorithm, which claims priority to a U.S. provisional application identified by serial No. 60/049,461, filed on Jun. 12, 1997, the disclosures of which are incorporated herein by reference. Notice that, by definition, an <L, W> pattern has at least L residues.

Further, given a pattern P and a sequence S, any substring of S that belongs to G(P) is called a matching site for P. The offset list of P contains the offsets of the first character of all matching sites of P.

Given the above definitions, we can now provide a general description of a preferred approach to improved sequence homology detection according to the invention, for example, in association with system 100 (FIG. 1). Sequence homology detection comprises two distinct phases: information gathering and searching.

First, before any search is performed, the underlying database D is mined. This mining procedure is also referred to as information gathering or dictionary formation. During this step all the significant <L, W> patterns are gathered and each such pattern P is associated with its offset list $L_D(P)$ (the particular criterion used for deciding if a pattern is significant or not is detailed in the search engine section).

The second step is the actual search. Given a query sequence Q, we identify all the patterns P (among those collected in the first phase of the process) which are matched by Q. For every such P, we pair together the region(s) of Q which match P with the corresponding regions of all the database sequences that also match P (these regions are easily accessible through the offset list $L_D(P)$). Finally, the paired regions are extended and aligned in both directions and scored by the use of a (user-defined) mutation matrix and the highest scoring matches are reported along with the implied alignments.

It is worth pointing out here that the information gathering phase is an one-time computation over D. The results obtained are stored in a file (pattern dictionary 120 of FIG. 1) and used every time that a search session is performed over the database D.

A motivation behind using patterns for describing related polypeptides lies on biological facts. In particular, it is known that there is a number of basic elements (either of structural nature like alpha helices, beta strands, loops, etc., or larger, functional units like motifs, modules and domains) which are the building blocks that proteins are made of. One of the key mechanisms used by evolution for differentiating among species is the mutation of amino acid positions in a protein sequence. Functionally/structurally important regions, though, are more resistant to such mutations. It is then reasonable to expect that such biologically related polypeptides can be identified by discovering: (a) conserved positions in their primary structure; and (b) an increased degree of reusability. In our terminology, these properties correspond to patterns with unexpectedly high support.

However, it is important to reiterate that the inventive search engine methodology described herein may be utilized with other known pattern dictionaries. Likewise, the inventive dictionary formation methodology may be employed to create pattern dictionaries for use with other known search engines.

It is to be appreciated that both methodologies are described below in sections II and III, respectively. While the dictionary formation method is applied before the search method, for the sake of facilitating the explanation, we discuss the processes in reverse order, starting with the search engine method and followed by the dictionary formation method.

II. Search Engine

Figures 4, 5:
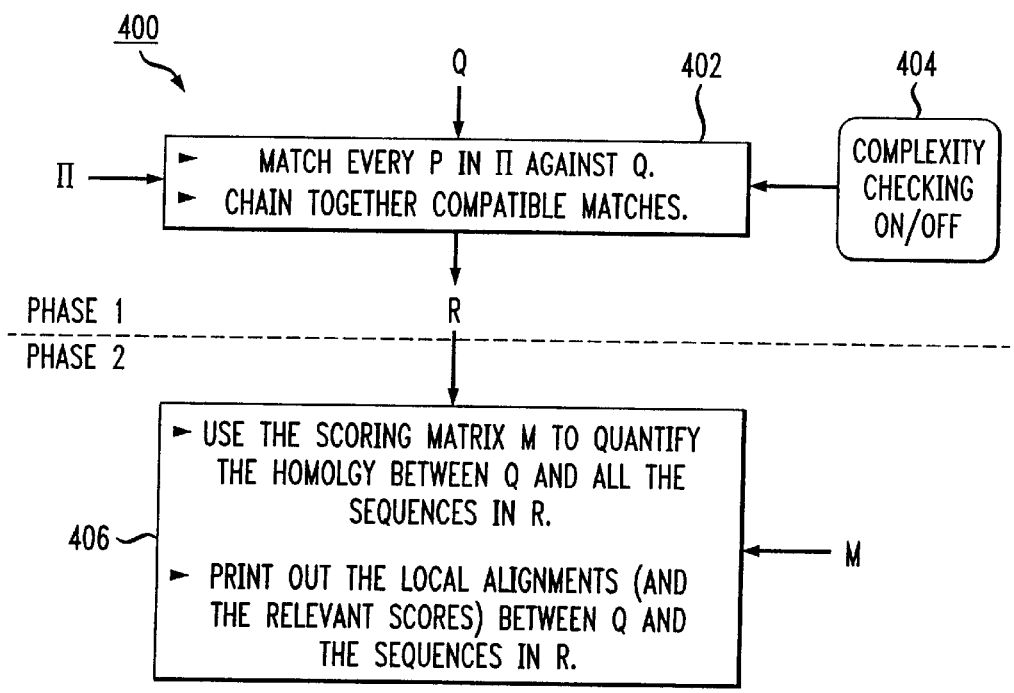
FIG. 4 is a high level flow chart illustrating a search engine methodology according to one embodiment of the present invention.
FIG. 5 is a diagram illustrating an example of a pattern matching process for a given query sequence according to one embodiment of the present invention.

Referring now to FIG. 4, a high level flow chart illustrating a search engine methodology according to one embodiment of the invention is shown. This methodology may be employed by the search engine 110 in FIG. 1. The operation of the search engine can be broken down into two distinct phases: (i) pattern matching+chaining (block 402); and (ii) scoring (block 406).

The first phase checks every pattern P in Π (recall that Π refers to the pattern dictionary 120 mentioned above) against the query sequence Q, isolating all the patterns that match Q. Below we describe a specific algorithm for performing this "check for a match" process; however, any matching algorithm can be used. Notice the "Complexity Checking" (block 404) of phase 1 in FIG. 4. In some cases, it is possible that a pattern P matches the query Q and yet it is undesirable to take this match into account. Such examples are the so called "low-complexity" patterns. Such patterns arise sometimes due to the nature of biological sequences. Low-complexity patterns are comprised almost exclusively of the same amino acid, e.g., the pattern "A.A . . . AAA.A.A" and appear because some proteins have long regions of repeating amino acids. Such patterns, though, are not considered important for homology detection purposes and it may be better to ignore any matches induced by these patterns. The decision to do so or not is left to the system users, by allowing them to set a "complexity-checking" component within the search engine to its "ON" or "OFF" state. For now, it is enough to remember that in the case when this component is set to "ON," some patterns in P will be ignored even though they match the query protein Q. Below we will give a description of the precise conditions under which a pattern P matching Q is ignored when the complexity checking is "ON."

Continuing with phase 1, every pattern P that matches Q generates a local homology between Q and all the database regions also matching P. Those latter regions are easily accessible through the offset list $L_D(P)$ of P. Assuming that P matches Q at offset i, every region (j, k) in $L_D(P)$ gives rise to the segment (i, j, k, l), where l is the length of the pattern P. This is explained in detail below. Finally, as the matching process goes on, compatible segments get chained together, forming longer segments (the notion of compatible segments as well as the operation of chaining will be explained below). At the end of phase 1, we are left with a set R containing all the sequences of the database D that match at least one pattern P in Π such that P also matches Q. Each sequence S in R is accompanied by the segments that describe the pattern-induced homologies between Q and S.

Consider the example that we introduced above. The query sequence Q=JLANQFTLMDPQDLA, matches both the patterns P1="A.Q.T" and P2="M.PQ" in Π. Given that P1 matches Q at offset 3 and P2 matches Q at offset 9, these 2 matches give rise to the following 4 segments:

(3, 1, 1, 5) (3, 2, 4, 5) —from $L_D(P1)$ (9, 1, 8, 4) (9, 3, 3, 4) —from $L_D(P2)$ and the set R is:

R={$s_1$—(3, 1, 1, 5) (9, 1, 8, 4)

$s_2$—(3, 2, 4, 5)

$s_3$—(9, 3, 3, 4)} where each sequence $s_i$ in R carries along a list of segments. Notice that in this particular example no chaining was possible.

The second of the phases of the search engine methodology depicted in FIG. 4 assigns a score to every sequence S in R. There are a number of approaches for computing this score for a given $S_j$. Each one, though, starts by scoring all the segments carried along by $S_j$. Each segment receives a score (these scores are called segment scores). The scoring is performed based on a mutation matrix M. Mutation matrices are 20×20 arrays of reals. The (i,j)-th entry of such a matrix indicates the probability that the i-th amino acid has changed during evolution to the j-th amino acid. For our purposes here, it suffices to assume that M is a function from Σ×Σ→R which, when given two amino acids A1, A2 as input, returns a real number. Since there are many mutation matrices that may be used, the user is given the option of choosing the particular matrix M to use.

For example, assume that we are using the unary mutation matrix M, i.e., M(A, A)=1 for all amino acids A, and M(A,B)=0 for all distinct amino acids A, B. Consider the first sequence in the set R above, namely the sequence $s_l$ which carries along the segments (3, 1, 1, 5) and (9, 1, 8, 4).

We show how to score the first of these two segments (the other one, as well as all segments in the set R are scored similarly). Imagine that we have aligned (one under the other) the two protein regions of length 5 implied by the segment, i.e., the region starting at offset 3 of Q and at offset 1 of $s_1$:

ANQFTL (from Q)

ARQSTL (from $s_1$)

The score of the segment is then computed by summing over all the aligned columns the values M(X,Y) where X, Y are the two amino acids aligned together under any given column. For the segment above, this score is:

$$M(A, A)+M(N, R)+M(Q, Q)+M(F, S)+M(T, T)+M(L, L)=1+0+1+0+1+1=4.$$

The scoring scheme described above for the segments is a basic scoring scheme. That is, the system user can set a number of options to modify the way in which the segment score is computed. For example, if the system parameter extend (which is an integer and is described below) has been set to a value larger that 0, the scoring takes into account not only protein regions described by the segment, but also an area of extend amino acids left and right of the two regions (the scoring proceeds exactly as described above, only that now longer regions are considered). Furthermore, if a gapped_alignment option has been set, then in the alignment of the extended regions (i.e., those regions left and right of the basic segment) we also use gaps in order to maximize the alignment score.

At the end of the above process (independent of which scoring variant is used), a segment score will have been computed for every segment in the set R. These segment scores are then utilized for the final step of the scoring phase, namely, quantifying the amount of similarity between Q and all the sequences $S_j$ in R. This quantification is performed by assigning a score to every $S_j$ in R; this score is called the sequence score for S (in order to distinguish it from the segment scores). Ideally, the higher the sequence score is for a sequence $S_j$, the more similar this $S_j$ should be to Q.

In scoring $S_j$, we only consider the segment scores of the segments that $S_j$ carries along. There are, again, several options. In the simplest case, the sequence score for $S_j$ is defined as the maximum among all the segment scores for the segments of $S_j$. A second, more involved approach is described below. Here, a directed graph is first built for the sequence $S_j$ being scored. The vertices of this graph are all the segments that $S_j$ carries along. Every vertex is assigned the segment score of the segment corresponding to that vertex. An edge is placed from the segment (i, j, k, l) to the segment (i', j, k', l') if i<=i' and k<=k', i.e., if the relative order of the two query regions described by the two segments (the regions Q[i ... i+l'−1] and Q[i' ... i'+l'−1]) is the same with the relative order of the two regions on $S_j$ described by the two segments (the regions $S_j$[k ... k+l−1] and $S_j$[k' ... k'+l'−1]). As with the vertices, every edge is also assigned a score, representing how regular is the displacement of the regions in the query (i.e., the difference i'−i) relative to the displacement of the regions on $S_j$ (i.e., the difference k'−k). The larger the difference between the displacements (i.e., the number | (i'−i)−(k'−k) |), the smaller the score of the edge. After the graph has been built, we can apply any standard longest path algorithm for identifying the path with the highest score (the score of a path is defined as the sum of all vertex and edge scores in the path). This score then becomes the sequence score for $S_j$.

Above, we have described several ways of computing both the segment and the sequence scores. In general, any other "biologically reasonable" scoring scheme can be used in their place.

Figure 6:
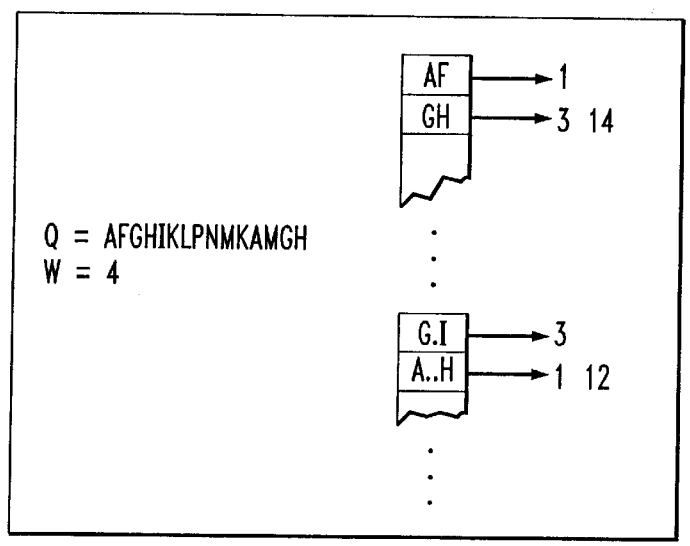
FIG. 6 is a diagram illustrating an example of a hash table generated for a particular query sequence according to one embodiment of the present invention.
Figure 7:
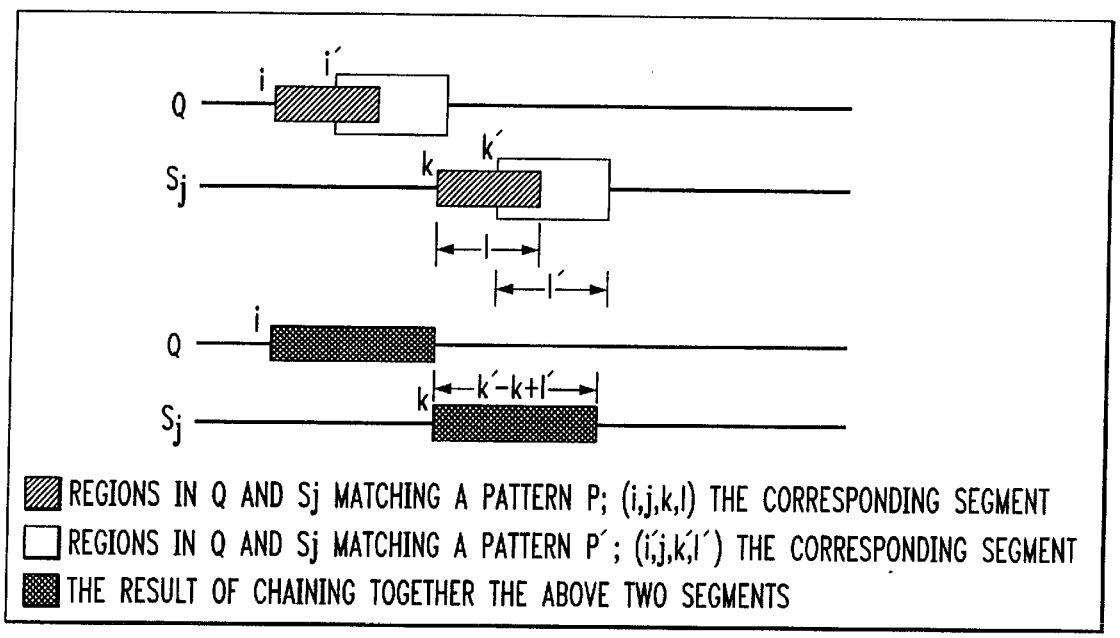
FIG. 7 is a diagram illustrating an example of a chaining process for a given query sequence according to one embodiment of the present invention.

Referring now to FIGS. 5, 6 and 7, more specific examples of the pattern matching, chaining and scoring processes of the search engine methodology 400 will now be explained. Again, during the search phase implemented by search engine 110, query proteins Q are provided to the system and database sequences S∈D similar to Q are identified and reported back to the user. The searching phase utilizes a set Π of patterns obtained by mining the input database D. For the purposes of the example here it is sufficient to assume that Π is a set of <L, W> patterns of the form described in the "Definitions" section above. Each pattern P∈Π is accompanied by its offset list $L_D(P)$ and has support at least $K_{min}$ in D. The numbers L, W and $K_{min}$ are parameters of our preferred method and the way in which they are set will be described below in the "Dictionary Formation" section.

The first thing to do when a query sequence Q is provided to the system is to locate all P∈Π that are matched by Q. This can be done very fast by using a hashing variation of a technique presented in D. Gusfield, "Algorithms on strings, trees and sequences: Computer Science and Computational Biology", Cambridge University Press, 62–63, 1997. More specifically, for every position within Q we generate W hash values, one for every substring of length 2, 3, ... , (W+1) starting at that position. For every such substring, the corresponding hash value depends only on the first and last characters of the substring, as well as on the number of residues in between these two characters.

FIG. 5 provides an example of the process for a given query sequence. In the example, the hash values generated for the W=4 substrings starting at position 6 of the sequence Q are shown. The hash value used for a substring s is:

$$H(s)=((av(\text{first\_Char})-av(\text{'A'}))+(av(\text{last\_char})-av(\text{'A'}))*26)*W+\text{gap}$$

where av(c) is the ASCII value of the character c, first_char and last_char are the first and last characters of s respectively and gap is the number of residues in between the first and last characters of s. Notice that because of the <L, W> density restriction, the gap is always less than W.

The hash entry corresponding to a particular value h contains all the offsets p of the query sequence Q such that a substring (of length at most W+1) starting at p hashes to the value h. FIG. 6 gives an example of the hash table generated for a particular query sequence. In FIG. 6, a snapshot of the hash table generated for the sequence Q=AFGHIKLPNMKAMGH is shown. Instead of using actual numeric hash values in order to label the table entries, we use a pattern describing all the strings that hash to a particular hash value. Each hash entry points to a list of offsets. Every offset in that list marks the beginning of a substring in Q which hashes to the relevant hash entry.

In order to check if a pattern P∈Π is matched by Q we use an array of counters C[1 ... |Q|] of size equal to the length of Q. Initially, every entry of the array is set to 0. Starting at offset 1 in P, we locate all offsets j within P corresponding to a residue, excluding the offset corresponding to the last residue. For every such j, let F be the shortest substring of P starting at j and containing exactly two residues. Let OL denote the list of offsets in Q pointed to by the hash table entry corresponding to F. If OL is not empty, then for every offset p∈OL, the counter C[p−j+1] is incremented by one. If the pattern P contains exactly n residues, then at the end of this process the counter C[i] will have the value (n−1) if and only if Q matches P at offset i. An advantage of the matching technique described above is that it typically requires time which is sublinear to the size of the query sequence Q and only depends on the number of residues in the pattern P.

Once a pattern P∈Π is found to be matched by a substring of Q starting at offset i, we need to relate that substring of Q with all the data base regions also matching P. This is easily done by scanning the offset list $L_D(P)$ which contains exactly these regions. More specifically, each entry (j, k)∈$L_D$(P) indicates that the substring starting at offset k of the j-th database sequence $S_j$ is an element of G(P). The local similarity between the query sequence Q and the database sequence $S_j$ is then registered as a quadruplet (i, j, k, l), called a segment, which gets associated with $S_j$. The number l=|P| is the length of the local similarity.

Sometimes, two distinct patterns P and P' matching both Q and a database sequence $S_j$ correspond to the same local similarity between Q and $S_j$. An example of such a situation is depicted in FIG. 7. In such cases, the individual segments corresponding to the two patterns must be chained into one. In particular, two segments (i, j, k, l) and (i', j, k', l') associated with $S_j$ are called compatible if and only if:

$$k <= k' \text{ and } k+l+w\_len > k' \text{ and } k'-k=i'-i$$

where w_len is an integer parameter defined by the user; w_len allows for the chaining of segments which are not intersecting as long as one starts no more than w_len positions after the end of the other. The segment resulting from chaining (i, j, k, l) and (i', j, k', l') together is:

$$(i, j, k, \max(l, k'-k+l'))$$

Chaining of compatible segments takes place every time that a new segment gets associated with a database sequence $S_j$, as the result of locating a pattern P∈Π matched by both Q and $S_j$. If there are segments already associated with $S_j$ which are compatible with the newly arriving segment, then the relevant pair of the new and the existing segment is discarded and gets replaced by the outcome of their chaining.

Having identified all the local similarities between Q and the database sequences, we are left with the task of evaluating these similarities. This is done by assigning a score (using a user defined scoring matrix) to every database sequence $S_j$ that is associated with at least one segment. Several options are available for the scoring function. One of ordinary skill in the art will appreciate other ways to score given the inventive teachings herein.

As mentioned above, one approach is to score each segment of $S_j$ individually and assign to $S_j$ the highest of these scores. Scoring a segment(i,j, k, l) can be done in either of two ways:

no gaps allowed: in this case the score is computed from the ungapped alignment implied by the segment, namely, the alignment of the regions Q[i, i+l−1] of the query and $S_j$[k, k+l−1] of the sequence. Furthermore, the user is given the option to extend the alignment "around" the segment by setting the variable extend. If this value is greater than 0, then the score is computed from the ungapped alignment of the regions Q[i−extend, i+l−1+extend] and $S_j$[k−extend, k+l−1+extend].

allowing gaps: this option is available only when extend >0 and permits for a finer scoring of the area around the segment, by allowing for gaps in that area of the alignment.

Figure 8:
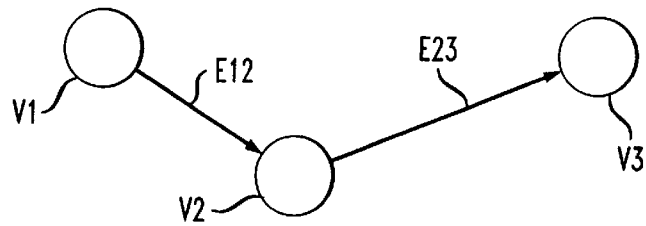
FIG. 8 is a diagram illustrating an example of a directed, weighted graph generated in accordance with a scoring process for a given query sequence according to one embodiment of the present invention.

As mentioned above, other scoring options are also offered, taking into account the relative order of the segments associated with the database sequence $S_j$ currently being scored. One approach after scoring each segment individually as described above, is to build a directed, weighted graph, as shown in FIG. 8. The vertices V of this graph are the segments associated with $S_j$ and there is a directed line between the segments (i, j, k, l) and (i', j, k', l') if:

i<=i' and k<=k'.

Every vertex is assigned a weight equal to the score of the corresponding segment, while every edge E is weighted based on: (a) how close the two segments are, i.e., the value of (i'−i−l); and (b) how regular is the displacement among the two segments, i.e., how much different (i'−i) is from (k'−k). The score of a path within this graph is the sum of the weights of all the vertices and edges of the path. The path with the maximal score is then computed and that score is assigned to $S_j$.

Figure 9:
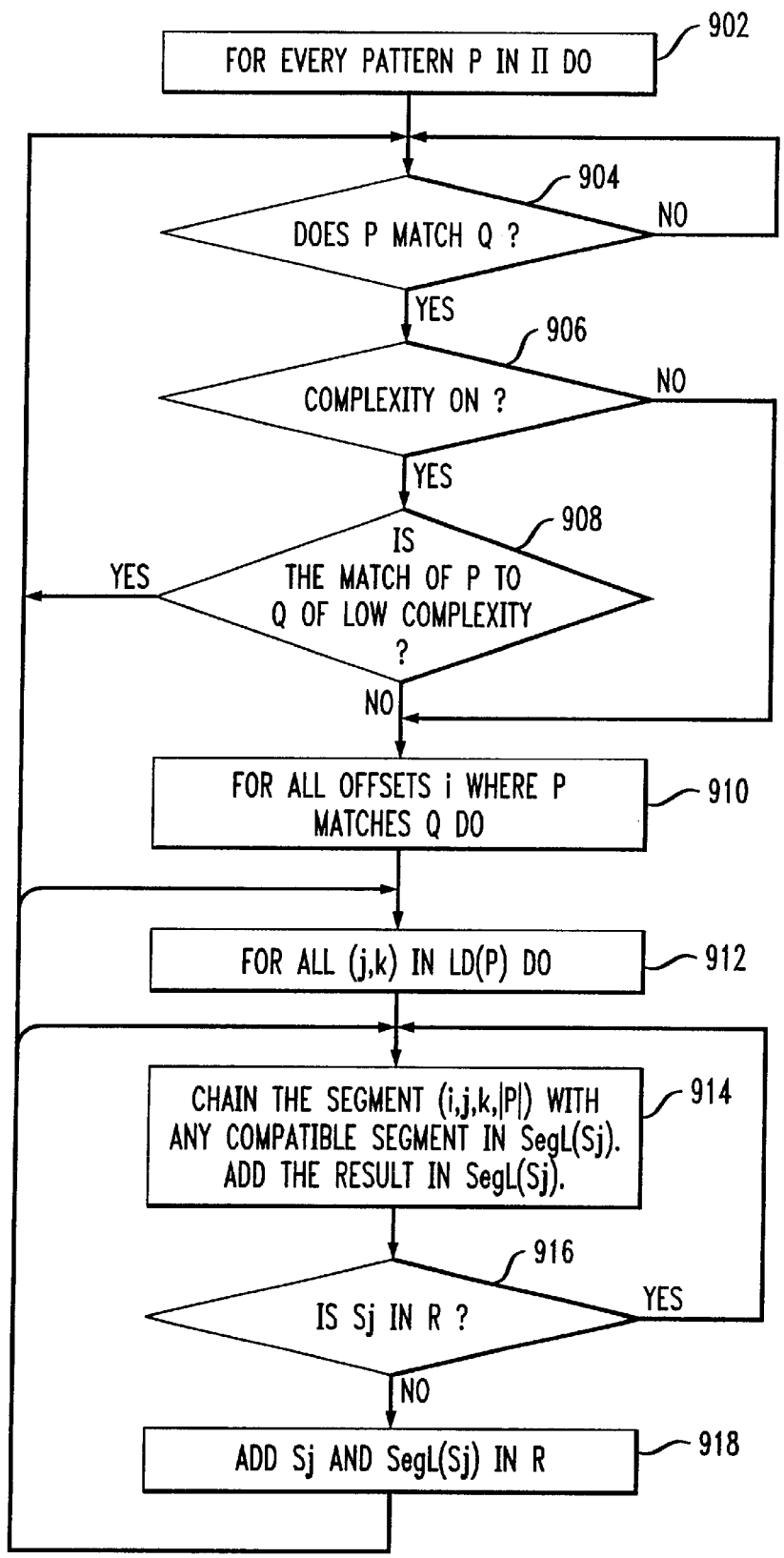
FIG. 9 is a flow diagram illustrating an embodiment of the matching and chaining phase of a search engine methodology of the present invention.
Figure 10:
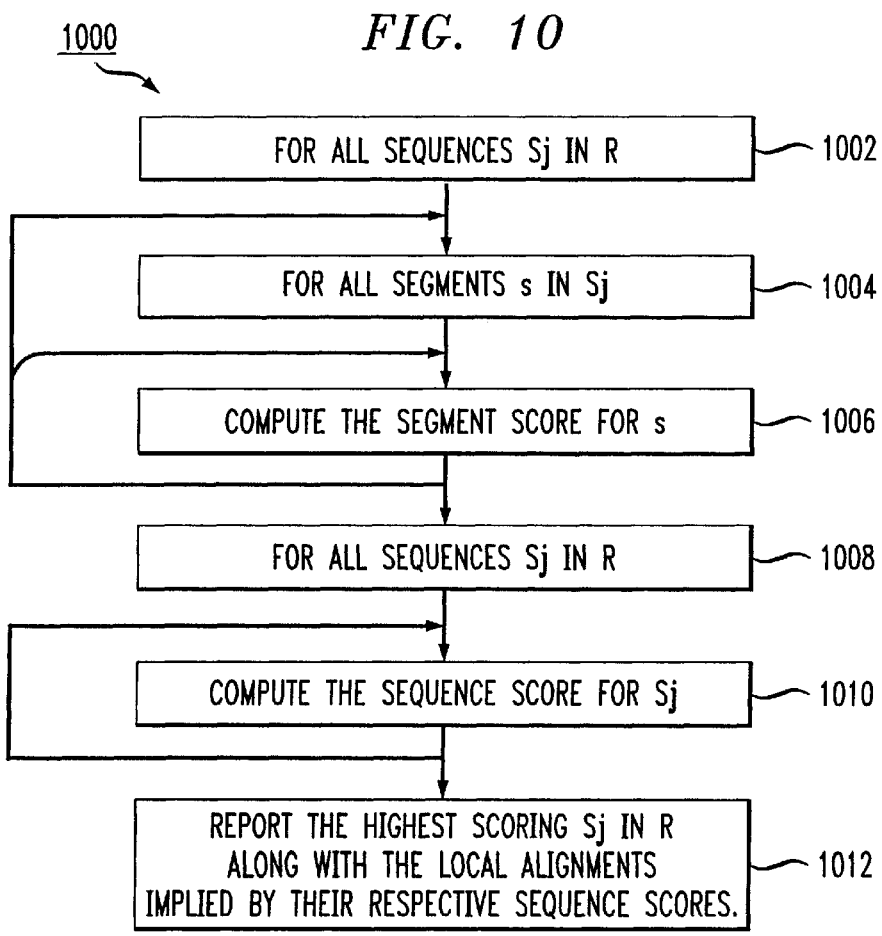
FIG. 10 is a flow diagram illustrating an embodiment of the scoring phase of a search engine methodology of the present invention.
Figure 11A:
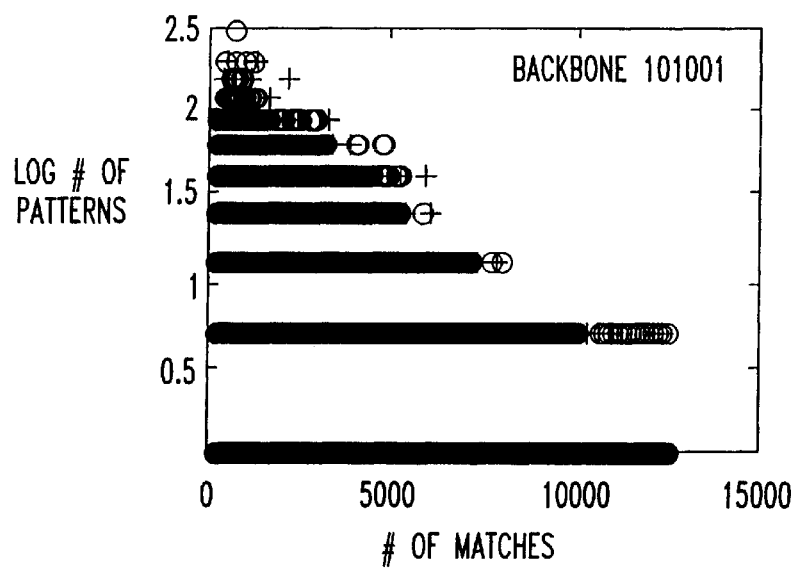
FIG. 11 is a diagram illustrating a distribution of patterns with given backbone structures in SERF and comparison with the random distribution of the same backbones.
Figure 11B:
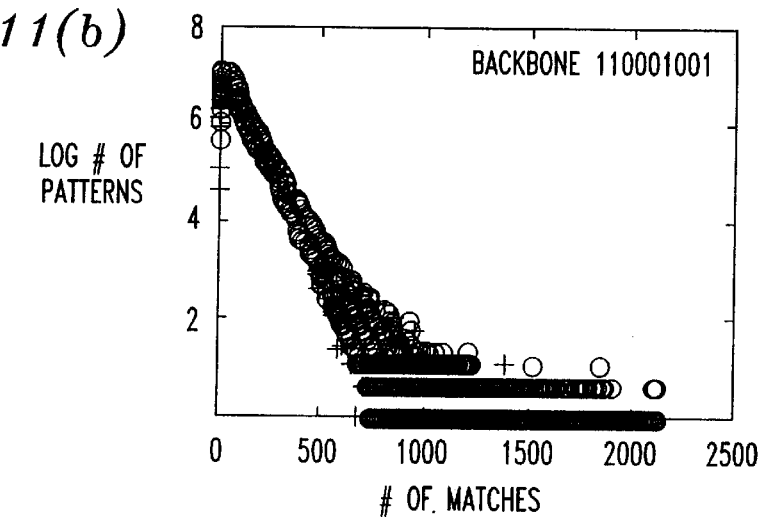
Figure 11C:
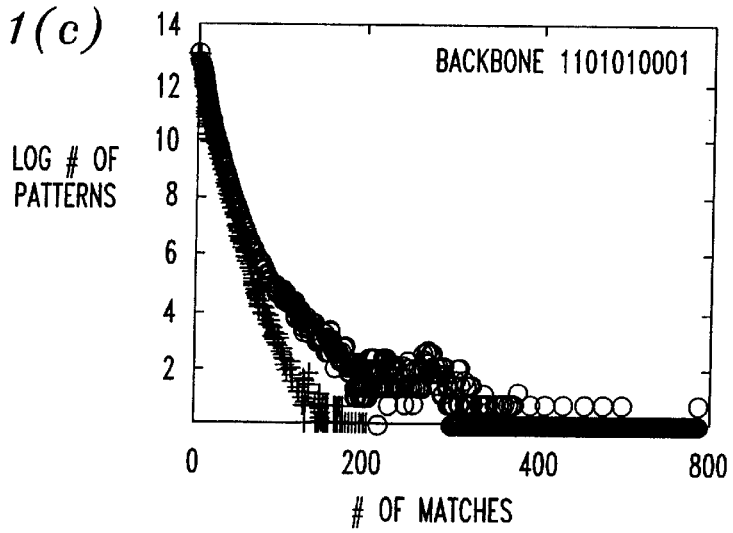
Figure 11D:
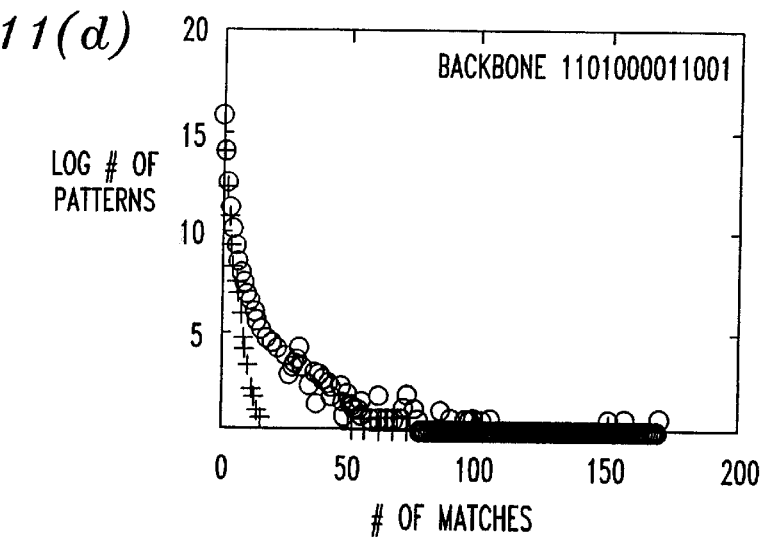

Referring now to FIGS. 9 and 10, respective flow charts summarily illustrate embodiments of the two phases performed by a search engine module of the invention. FIG. 9 depicts an embodiment 900 of the matching and chaining phase, while FIG. 10 depicts an embodiment 1000 of the scoring phase.

In FIG. 9, it is assumed that every sequence $S_j$ in the database D has an associated list of segments SegL($S_j$). Initially, all these lists are empty. Also, the set R is initially empty. As the computation described by the flow chart of FIG. 9 proceeds, R is populated by sequences $S_j$. As such a sequence gets inserted into R, it brings along its segment list SegL($S_j$).

Thus, for every pattern P in Π (block 902), the search engine performs does the following operations. In step 904, the search engine determines whether P matches Q. If no, then go to the next P in the dictionary. If yes, in step 906, the search engine determines whether the complexity checking component has been enabled by the user. If it has been enabled, in step 908, the engine determines is the match of P to Q is a low complexity match (to be explained in greater detail below). If yes, then the engine goes to the next P in the dictionary. If no, then, for all offsets i where P matches Q (bock 910) and for all (j, k) in $L_D$(P) (block 912), the engines performs the following operations. In step 914, it chains the segment (i, j, k, |P|) with any compatible segment in SegL ($S_j$). Then, the engine adds the result in SegL($S_j$).

In step 916, the engine determines whether $S_j$ is in R. If yes, then the engine returns to step 914. If no, then the engine adds $S_j$ and SegL($S_j$) in R. Steps 914 through 916 are performed for all offsets i where P matches Q and for all (j, k) in $L_D$(P). The entire process (steps 904 through 916) is repeated for every P in the pattern dictionary.

Now that matching and chaining has been performed, the search engine the scoring operations in FIG. 10. So, for all sequences $S_j$ in R (block 1002) and for all segments s in $S_j$ (block 1004), the engine computes a segment score for s, in step 1006. Then, for all sequences $S_j$ in R (block 1008), the engine computes a sequence score for $S_j$, in step 1010. Lastly, in step 1012, the engine reports the highest scoring $S_j$ in R along with the local alignments implied by their respective sequence scores.

Referring again to FIG. 4 and as previously mentioned, the search engine module 110 may include a complexity checking component (e.g., step 906 of FIG. 9). The complexity checking component is responsible for discarding local homologies generated because of low complexity regions. First, the low complexity checking happens in two phases: both during the dictionary building phase ("Dictionary Formation" section) as well as in the Searching phase (this section).

During the dictionary building phase, low complexity regions are dealt with in two ways. First, when looking for patterns in the input database, we disregard (i.e., remove from the input) all protein regions that constitute of L or more consecutive appearances of the same amino acid (L is an integer parameter that we set during the dictionary building phase; for our purposes here it suffices to assume that it has some fixed value). This takes care of low complexity regions like the one shown in boldface below (the dots indicate that there are more amino acids left and right of the depicted string):

......ASDFHRTYIUSFFFFFFFFFFFFFFFFFFFAKJRBVCJ.....

This is, however, just one case of a low complexity region. Many more exist. Consider, for example, the bold-faced part of the following region:

GFWRETIOJIFPAPAPAPAPAPAPAPAPAPAPAPAPAJSHDGF....

To deal with regions of that sort (i.e., of a generalized repetitive composition), we also discard all overlapping appearances of a given pattern P. In other words, if the pattern P matches the database sequence Sj at the offsets $k_1$ and $k_2$ (where $k_2 > k_1$) and $k_2 - k_1$ is less than the length of P, then neither offset is placed in the offset list $L_D(P)$ of the pattern P. For example, in the region shown above, the pattern "P.P.PA" which has a length of 6, appears (among other places) at offsets 12 and 14, i.e., at overlapping positions, since 14−12=2 and 2<6.

During the search engine phase now, we have two ways of capturing and discarding low complexity homologies. The first one is a generalization of the example given above. In short, we would like to discard all patterns that are not "linguistically rich," i.e., they exhibit an over-representation of one specific amino acid. For that purpose, we allow the user to set the value of a parameter V (a real between 0 and 1). A pattern P matching the query sequence Q will be further considered only if a variability v(P) of P is no more than the value V. In particular, for each pattern P, we define its variability v(P) as:

$$v(p) = \frac{\max_R \{\text{number of times that the residue } R \text{ appears in } P\}}{\text{total number of positions in } P \text{ covered by residues}}$$

Even after passing the variability test described above, a second level of checking follows. This second level intends to capture a more subtle notion of low complexity. To understand how it works, consider the following example. Let us assume that the query protein Q is the following simple string:

Q=FRGDSAAABBBBAABBSJIEKL and let us consider the pattern P="A . . . B . . . AB". The pattern matches the query at offset 7, as shown below:

```
          A...B..AB
     FRGDSAAABBBBAABBSJIEKL
```

The region of the match and its immediate surrounding is a low complexity region (it is comprised of just 'A's and 'B's). The pattern P, however, has a variability of just 0.5. To deal with low complexity regions of this character, we allow the user to define integers margin and $min_{13}$ m (where $min\_$ m<=2*margin) as well as a percentage perc. We then check for approximate matches of the pattern under consideration (here the pattern "A . . . B . . . AB") in margin characters left and margin characters right of the actual matching site (here the offset 7 of the query). A pattern P matches approximately at a given offset of the query if, when placed at that offset, at least perc % of the regular characters in the pattern match the underlying characters of the query. For example, if perc =75%, then the pattern "A . . . B . . . AB" approximately matches Q at offsets 6 and 8, as shown below:

```
       A...B..AB
  FRGDSAAABBBBAABBSJIEKL     (at offset 6)
        A...B..AB
  FRGDSAAABBBBAABBSJIEKL     (at offset 8)
``` since, in each of these offsets, 75% of the pattern regular characters (i.e., 3 out of the 4) match the corresponding query characters. Having defined the parameters margin, min__m and perc, we are now ready to say when a pattern induced local homology between the query and a database region is deemed of low complexity during this level of checking. Consider that a pattern P matched the query Q at offset X and a database sequence S at offset Y. The matching will be considered of low complexity if either of the following is true: (i) the pattern matches the query Q approximately in at least min__m of the 2*margin characters left and right of X.; or (ii) the pattern matches the sequence S approximately in at least min__m of the 2*margin characters left and right of Y.

III. Dictionary Formation

As previously mentioned, in a preferred embodiment, the dictionary formation methodology is performed prior to a the search engine receiving a query sequence from a user. This is because, referring again to FIG. 1, the search engine module 110 preferably utilizes the pattern dictionary 120 formed by the dictionary formation module 130. The dictionary formation module 130 implements the inventive database processing methodology that is explained below to form the pattern dictionary (or bio-dictionary). However, also as previously mentioned, the pattern dictionary 120 may be used by search engines other than the one described herein. That is, existing search engines may utilize the patterns mined from a source database in accordance with the invention. Nonetheless, in accordance with a preferred embodiment, it will be assumed that the pattern dictionary formed according to the inventive methodology described herein will be used by the inventive search engine also described herein.

During the dictionary formation phase (also referred to as an information gathering phase), the set Π of all the significant <L, W> patterns found in the database D under consideration is determined. This is, in essence, a data mining procedure in which D is exploited with the intention to discover hidden relationships among the sequences of D. The idea is to focus on those relationships which are considered unexpected and by virtue of that quality they are also presumably of biological relevance. For our purposes, the significance of a pattern will be described by its support within D. More specifically, we will seek to define the number $K_{min}$ (the minimum support) such that every pattern with support at least $K_{min}$ can be shown to be statistically important. All such patterns (along with a few exceptions which do not abide by the minimum support requirement) will be. included in the set Π, the input to the search phase.

Recall that the concept of $K_{min}$ was first introduced above in the "Definitions" section. Also, the concept of "density" was also introduced. Recall, that density describes the minimum amount of homology between any two members of G(P) (where G(P) refers to the language of polypeptides consisting of all strings that can be obtained from P by substituting each don't care character by an arbitrary residue from $\Sigma$) and is defined by two integers L and W (L$\leq$W): a pattern P has an <L, W> density if every substring of P that starts and ends with an amino acid and has length at least W contains L or more residues. Again, these parameters are described in the above-incorporated U.S. patent application identified by Ser. No. 09/023,756, filed on Feb. 13, 1998, directed toward the "TEIRESIAS" algorithm.

While a preferred methodology of the invention utilizes parameters L and W in forming the pattern dictionary Π, it is to be appreciated that other known techniques for determining the minimum amount of homology between any two members of a group of sequences may be employed.

Setting the values of parameters L, W and $K_{min}$ involves the consideration of a number of sometimes conflicting and interconnected factors. The ratio L/W, for example, describes the amount of homology allowed, during the search phase, between a query sequence and the proteins in D. A small L/W will permit the detection of weak similarities. Since several value pairs (L, W) lead to the same ratio L/W, what should the exact settings for L and W be? Opting for a large value of L will usually result in a long running time for the information gathering phase (unless L/W is close to 1). Furthermore, selecting a large L would ignore weak patterns with only a few amino acids, which are among the ones that are of interest (i.e., are usually missed by existing similarity searching tools). Selecting too small an L on the other hand (e.g., 2 or 3) may be useless since in that case the distribution of <L, W> patterns with L+i residues (for small i) in the input database D is not significantly different from the corresponding distribution in a random database with the amino acid composition of D. In the most general case, it is to be appreciated that the values L, W and $K_{min}$ can be chosen completely arbitrarily. However, in order to substantially guarantee that the discovered patterns are well above the level of statistical noise, we augment the pattern discovery process with a statistical framework (i.e., a way to set the parameters mentioned above).

Figure 13:
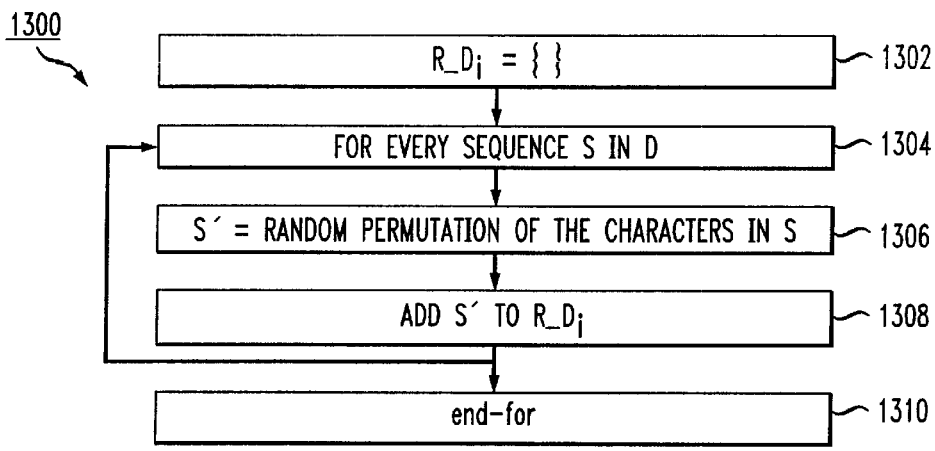

To make the above point more clear, consider FIG. 11 which compares the distribution of patterns in a test database known as SwissProt Rel. 34 or SP34 (see A. Bairoch and R. Apweiler, "The SWISS-PROT protein sequence data bank and its supplement TrEMBL in 1998", Nucleic Acids Res., 26:38–42, 1998) with the corresponding random distributions. FIG. 11 depicts a distribution of patters with given backbone structures in SP34 (the distributions being denoted by the "o" symbols) and comparison with the random distribution (the distributions being denoted by the "+" symbols) of the same backbones. Recall that the concept of a backbone was first introduced above in the "Definitions" section. A point (X, Y) in a curve indicates that there are exactly Y patterns (of the given backbone structure) such that each of these patterns has support X, i.e., it is matched by exactly X distinct database sequences. The results shown here were obtained using a "cleaned-up" version of SP34 (cleaning up of a database is explained below). For SwissProt, we computed the support of each <L, W> pattern with exactly L residues (for the values of L, W shown in FIG. 11). Then, the results were tabulated creating one row for each possible backbone: the i-th column of the row corresponding to a given backbone B indicates the number of patterns (of that backbone structure) with support i within SwissProt. The random distributions were obtained by following exactly the same approach for N=2000 randomly shuffled versions of SwissProt (FIG. 13 describes the shuffling process by which each one of the shuffled versions is obtained). In this case, the row for a given backbone B is obtained by averaging the rows corresponding to B in all the 2000 tables. As a result, the i-th column gives a sufficiently accurate estimate of the mean number of patterns with backbone B that appear in exactly i sequences within a random data base having the residue composition of SwissProt. In FIG. 11, we plot the SwissProt results of selected backbones against the distribution of the means for the same backbones. Although the results presented involve particular backbones, there is no qualitative change if other backbones are used.

Notice that we are using 2000 sampling points (the randomly shuffled versions of the input database). This is just for illustrative purposes. The actual number of sampling points can, in principle, be set arbitrarily. In general, as the number of such points becomes larger, the estimates that we obtain converge more accurately to their true values. Given any desired confidence level for the estimations to be computed, standard statistics theory can be used to decide how many sampling points to use.

As FIG. 11 implies, we start distinguishing the compositional bias (in terms of patterns) in SwissProt versus a random database only when L becomes 5 or larger. In general, the value of L will depend on the size of the underlying database D: the larger the database, the higher this value should be. The results shown for SwissProt have been obtained using the value L=6. For W, we chose the value 15, so that the ratio L/W (i.e., the minimum allowed homology) is 40%.

Having set the values of L and W it remains to decide what the minimum support $K_{min}$ should be. We focus only on patterns with exactly L residues since every larger pattern contains at least one subpattern with exactly that many amino acids. One approach is to select $K_{min}$ so that the probability of a pattern appearing in $K_{min}$ or more distinct sequences is small. A closer look at FIG. 11(d), though, reveals that this approach might be too strict. In particular, consider a support level of K=15. The random distribution indicates that one expects, by chance alone, between one and two patterns with support K. So, according to the aforementioned criterion, a pattern with support 15 within SwissProt would be deemed not important. However, the two distributions have a striking difference at that support level. In particular, while the mean of the random distribution at K=15 has a value of about 1.5, within SwissProt there are about 180 patterns with support 15.

So, it seems that if one considers the probability of a pattern in isolation the result will be to discard many patterns which, according to the above distribution, are above the level of noise. This observation prompts us to use a different criterion for significance.

Referring now to FIGS. 12 through 15, we present flow diagrams illustrating a preferred approach for determining a significance criteria. That is, we provide a methodology for computing the value of $K_{min}$. Given the value of $K_{min}$, the pattern dictionary Π is formed by including therein all patterns in the source database D that have at least that value $K_{min}$ as support. Thus, it is to be understood that the dictionary formation module 130 of FIG. 1 may perform the processes depicted in FIGS. 12 through 15.

Generally, in our approach, instead of looking at individual patterns, we consider together all the patterns of a particular backbone structure. More specifically, for any given backbone B and an underlying database D, let $N_{B,K}$ be:

$N_{B,K}$=number of patterns with backbone B which have support K within D. Also, let $X_{B,K}$ be the random variable (defined over the space of all shuffled versions of D) corresponding to $N_{B,K}$. The minimum support $K_{min}$ is then the first number K for which the following inequality is true:

$$\max_B \{Pr[X_{B,K} \geq N_{B,K}]\} \leq threshold$$

where threshold is a user defined probability imposing a level of confidence on the minimum support $K_{min}$ coming out of the above inequality. A smaller threshold leads to a larger value for $K_{min}$ and to a greater statistical importance for the patterns that will be eventually selected.

Thus, as inputs to the process for determining the significance criteria $K_{min}$, we have the source database D, the integer parameters L and W, an integer N representing a number of samples, and threshold which is a real number between 0 and 1. Of course, as the output of the process, we get the integer $K_{min}$, such that all patterns in D that have support $K_{min}$ or more are statistically important and therefore are included in the pattern dictionary to be searched upon receipt of a user query.

The following explanations of the flow charts uses various notation, some of which has been introduced above. However, for the sake of clarity, the following definitions apply. Given any pattern P, the backbone B(P) of P is defined as the string over {1, 0} obtained when replacing every regular character of P with '1' and every don't care character of P with '0,' e.g., if P=A . . . F.G . . . R, then B(P)=100101001. If B is an arbitrary backbone and P is a pattern such that B(P)=B, then we say that P is a B-pattern. $N_{B,K}$ is then said to be the number of B-patterns with support K in D, $X^i_{B,K}$ is the number of B-patterns with support K in the i-th random database. While $m_{B,K}$ is the average of all $X^i_{B,K}$ and $S_{B,K}$ is the variance of all $X^i_{B,K}$. It is to be appreciated that since we do not have an analytical description for the distribution of the random variable $X_{B,K}$, we employ standard sampling techniques. Thus, for a given database D, we are able to experimentally compute accurate point estimates for both the average (mean) $m_{B,K}$ and the variance (deviation) $S_{B,K}$ of the random variable $X_{B,K}$.

Figure 12:
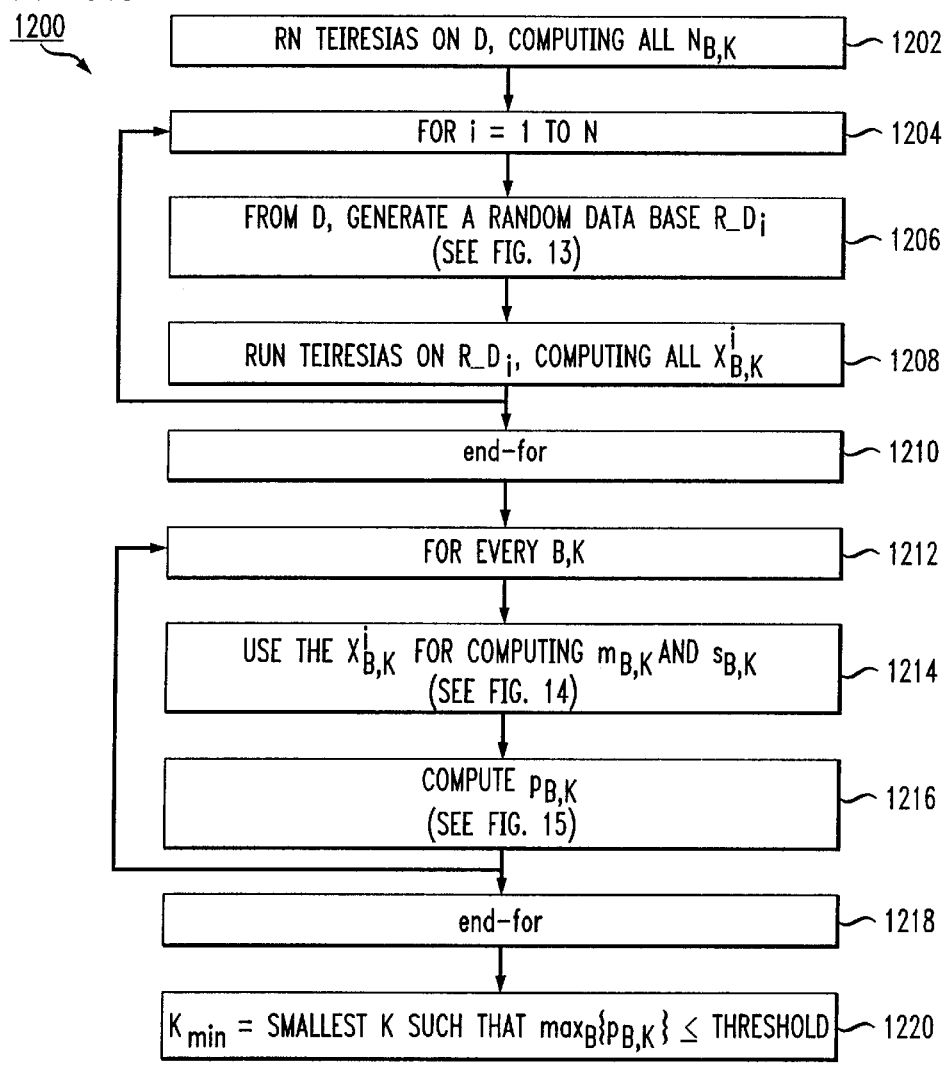
FIGS. 12 through 15 are flow diagrams illustrating a dictionary formation methodology according to one embodiment of the present invention.

Referring initially to FIG. 12, the overall process 1200 starts by running the TEIRESIAS algorithm (i.e., as described above and in the above-incorporated U.S. patent application identified by Ser. No. 09/023,756, filed on Feb. 13, 1998) on D and computing $N_{B,K}$, in step 1202. While the TEIRESIAS algorithm is preferred, it is to be understood that $N_{B,K}$ may be computed using other conventional techniques. Then for i=1 to N (block 1204), the following steps are performed.

In step 1206, a random database R_$D_i$ is generated. This step is further explained in the context of FIG. 13. As shown in process 1300, R_$D_i$ (block 1302) is generated by computing, for each sequence S in D (block 1304), a random permutation of the characters in S (step 1306). The random permutation of the characters in S is referred to as S '. S' is added to R_$D_i$ (step 1308). The process is repeated until every sequence S in D is processed (block 1310). Thus, R_$D_i$ includes all random permutations S'. Returning to FIG. 12, in step 1208, TEIRESIAS is run on R_$D_i$ in order to compute $X^i_{B,K}$. Steps 1206 and 1208 are for all i's, that is, until i=N (block 1210).

Figure 14:
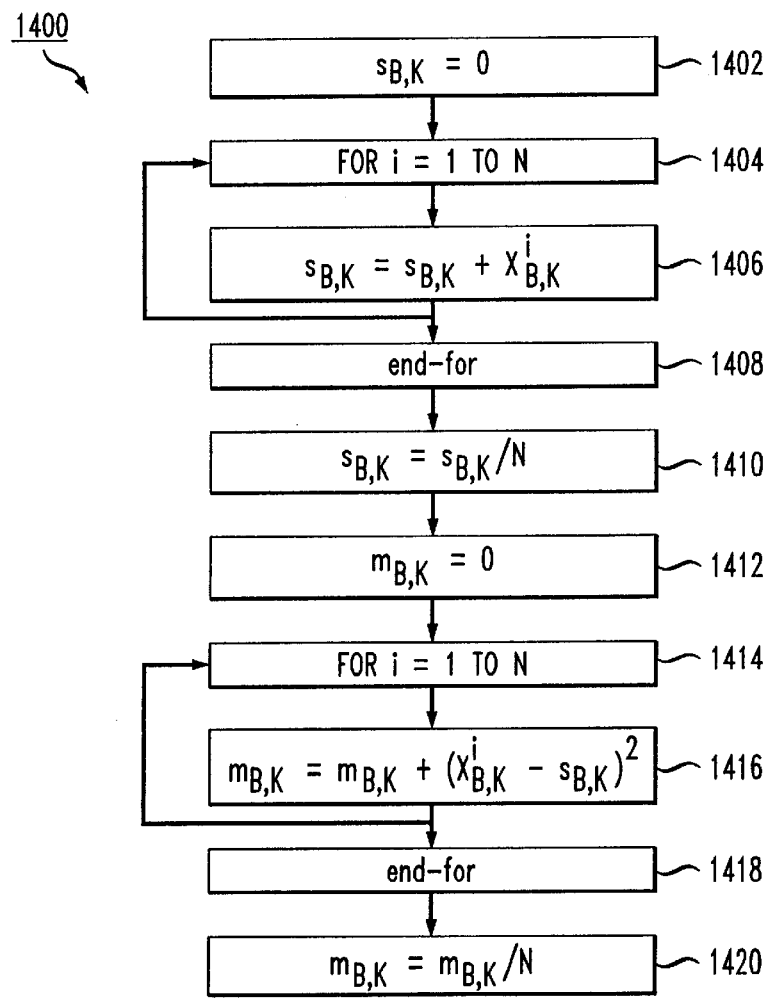

Then, for every B, K (block 1212), we use the $X^i_{B,K}$ for computing $m_{B,K}$ and $s_{B,K}$ This step is further explained in the context of FIG. 14. As shown in process 1400, $s_{B,K}$ is first set to 0 (step 1402). Then, for i=1 to N (block 1404), $s_{B,K}$ is computed as the sum of $s_{B,K}$ and $X^i_{B,K}$ (step 1406). The process is repeated for all i's (block 1408) and the mean $s_{B,K}$ is finally computed by dividing $s_{B,K}$ by N (step 1410). Then, the deviation $m_{B,K}$ is computed in steps 1412 through 1420. First, in step 1412, $m_{B,K}$ is first set to 0. Then, for i=1 to N (block 1414), $m_{B,K}$ is computed as the sum of $m_{B,K}$ and $(X^i_{B,K} - s_{B,K})^2$ (step 1416). The process is repeated for all i's (block 1418) and the deviation $m_{B,K}$ is finally computed by dividing $m_{B,K}$ by N (step 1410).

Figure 15:
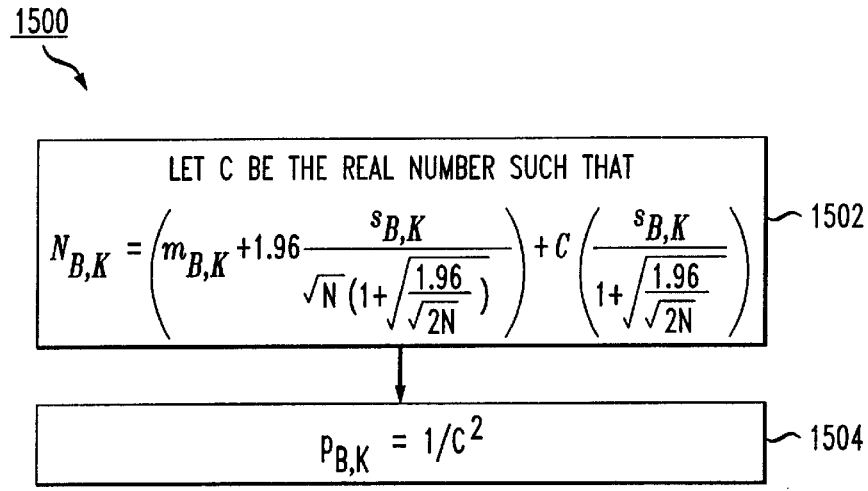

Returning to FIG. 12, in step 1216, $p_{B,K}$ is now computed using $m_{B,K}$ and $s_{B,K}$ This step is further explained in the context of FIG. 15. As shown in process 1500, a real number C is defined in step 1502, such that:

$$N_{B,K} = \left(m_{B,K} + 1.96 \frac{s_{B,K}}{\sqrt{N}\left(1+\sqrt{\frac{1.96}{\sqrt{2N}}}\right)}\right) + C\left(\frac{s_{B,K}}{1+\sqrt{\frac{1.96}{\sqrt{2N}}}}\right)$$

where N represents a particular number of samples or trials, e.g., 2000. Thus, in step 1504, $p_{B,K}$ is computed as being equal to $$\frac{1}{C^2}.$$

It is to be understood that $p_{B,K}$ is an upper bound for the probability $Pr[X_{B,K} > N_{B,K}]$. Thus, in summary, we use the sample mean and deviation of $X_{B,K}$ to compute C for the values Of $N_{B,K}$ at hand. It is to be appreciated that the constant C is associated with Chebychev's inequality, as is well known in the art of statistics. Note that the constant C is calculated using a confidence level of 95%, however, this is not a requirement. That is, any other value would be applicable as well.

Returning to FIG. 12, steps 1214 (FIG. 14) and 1216 (FIG. 15) are repeated for every B,K. Then, in step 1220, $K_{min}$ is determined to be the smallest K such that $\max_B\{p_{B,K}\}$<threshold. In the test case presented in the next section (SwissProt. Rel. 34), the value of threshold has been chosen so that $K_{min}$=15, i.e., the support level where only 1.5 patterns of a given backbone structure are expected by chance. There is a tradeoff: we are willing to allow a small number of pattern-induced local homologies which can be the result of chance (the 1.5 patterns above) in order to be able to capture the many more statistically important similarities implied by the other patterns at that same support level present within SwissProt.

Before providing some experimental results in the next section, we first explain the concept of cleaning up a database before performing the dictionary formation methodology of the invention. This process is depicted in FIG. 16 and also may be implemented by the dictionary formation module 130 of FIG. 1. Several databases contain groups of highly homologous sequences (e.g., the hemoglobin alpha chain proteins). Such groups not only slow down the pattern discovery process by introducing a huge number of patterns, but they can also spuriously elevate the significance of a pattern. This happens for patterns that appear many times within a family of highly homologous sequences and only occasionally outside of it.

In order to deal with these problems, a database D may be "cleaned up" before the pattern discovery process begins. As shown in FIG. 16, the cleaning up process 1600 involves identifying and grouping together highly similar proteins (step 1602). Two sequences are placed in the same group if after being optimally aligned the shorter one has X% of its positions (e.g., 50%) identical to that of the longer sequence. The resulting groups are called redundant groups. The set D' on which the information gathering process will be performed is comprised of: (a) those sequences in D which were not found to be sufficiently homologous to other proteins; and (b) the longest sequence from each of the redundant groups (step 1604). Finally, each of the redundant groups is separately processed by the TEIRESIAS algorithm (step 1606), collecting patterns until all the sequences of the group match at least one of these patterns. This approach guarantees that even groups containing multi-domain proteins are treated correctly, by generating at least one pattern per domain. It is worth pointing out that patterns resulting from the processing of the redundant groups will usually be quite dense (the number of residues is going to be much larger than the number of don't care characters) and long. This is a consequence of the high homology of the group sequences. For such patterns, we allow approximate matches during the search phase.

IV. Experimental Results

In this section we discuss experimental results associated with a preferred embodiment of the invention. That is, the following results have been generated by implementing both the dictionary formation (information gathering) and search engine methodologies of the invention, explained in detail above, in accordance with SwissProt Rel. 34 as the test database. A quantitative and qualitative description of the patterns discovered in the information gathering phase is given in the first subsection (A) below by analyzing the coverage that these patterns achieve for SwissProt and by annotating the most frequently occurring of them. In a second subsection (B) below, we present the results of the search phase on a number of query sequences.

A. Information Gathering

The treatment of SwissProt starts by cleaning it up as described in the previous section. The results of this process are detailed in FIG. 17. The clean-up process on SwissProt generates 9,165 redundant groups of highly similar sequences. The cleaned-up database (the one that the information gathering phase will operate on) is formed by removing the highly-similar sequences from the original input and then augmenting the resulting set by adding in it the longest sequence from each redundant group.

Having the cleaned up database available, all that is needed for TEIRESIAS to work on it is setting the values of the parameters L, W and $K_{min}$. As already explained, we use the settings L=6 and W=15. Further, in the results reported here we chose a threshold value of $10^{-11}$ and a confidence level of 95% in the computation of the deviations. The value of $K_{min}$ computed for these settings turned out to be 15. Running TEIRESIAS on the cleaned-up database with the values of L, W and Kin specified above generated a set Π (pattern dictionary) of 534,185 patterns.

Figure 19A:
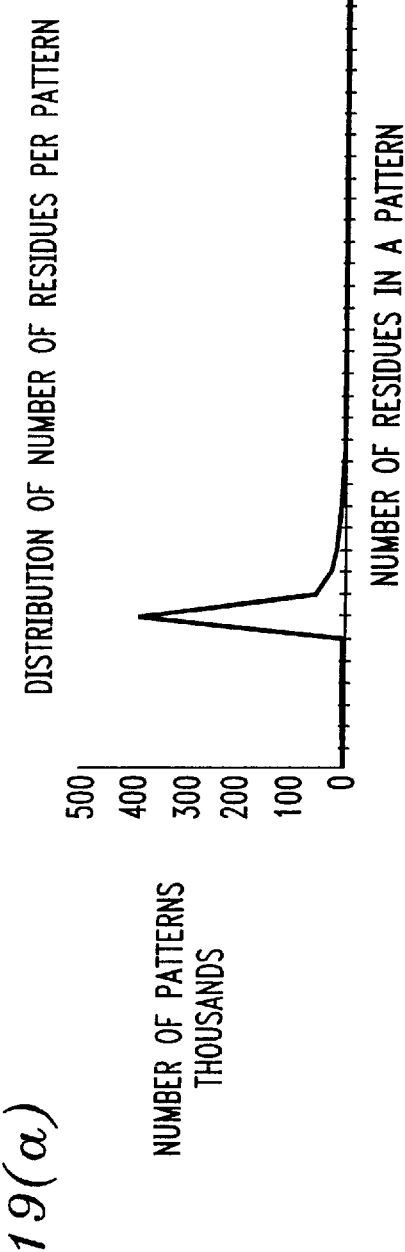
Figure 19B:
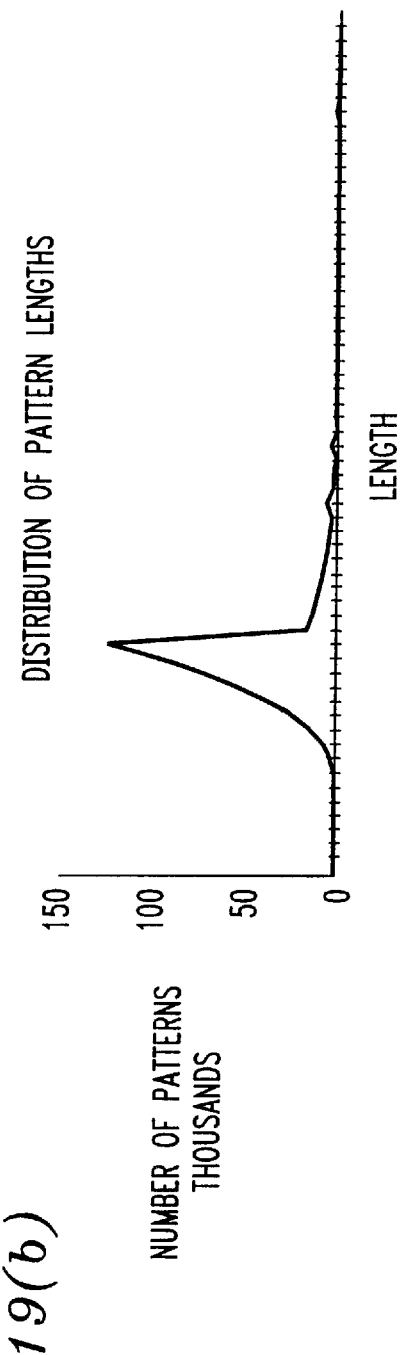

Mining the cleaned-up database is only the first step of the information gathering phase. It is also necessary to apply the pattern discovery process on the 9,165 redundant groups. Again, we use TEIRESIAS to treat each such group collecting enough <6, 15> patterns to make sure that each sequence in the group matches at least one pattern. These patterns are then added to the set Π in order to form the final set of patterns Π which will be used by the search phase. FIG. 18 provides information regarding the coverage achieved by these patterns over the entire SwissProt Rel. 34. The database regions covered by a pattern are exactly those substrings matching the pattern. Notice that for dense and long patterns (coming mostly from the processing of the redundant groups), we have allowed for approximate matches, where "most" of the pattern (specifically, 80% of the patterns' residues) is matched by a region. It is worth pointing out that most of the uncovered sequences are fragments. More specifically, only 231 have size more than 50. FIG. 19 gives distributions for the following characteristics of the patterns in Π: (i) length of the SwissProt Rel. 34 patterns; and (ii) number of amino acids or residues.

As exemplified in FIG. 18, one of the key goals for the success of the search phase to follow (namely the good coverage of SwissProt) has been achieved. The question that remains to be answered is if the patterns discovered are of biological relevance. In an effort to address this concern, we analyzed the most frequently occurring among these patterns. The resulting annotation is presented in FIG. 20. From this analysis, it is evident (at least for the patterns which were examined) that the pattern discovery process identifies sequence features that are biologically important.

FIG. 20 illustrates the 100 patterns with the highest support. Wherever possible, the patterns within a category were aligned with respect to one another. The lower case italics were used for convenience and are place-holders for the following bracketed expressions: a: [STGDAR], b: [STGDK], c: [STGDKY], d: [STGK], e: [GASMDL], f: [GISETV], g: [LIVMFY], h: [LIVMF], i: [LIVMA], j: [LIVMC], k: [LIVMF], l: [ILVMF], m: [QKCS], n: [KRQA], o: [IVTNF], p: [QKCASN], q: [QKIAGN], r: [RKAHQN], s: [KRQNE], t: [KRQMN], u: [LFYIMS], and v: [AGSPE]. A bracket indicates a position that can be occupied by any one of the residues in the bracket.

It is to be appreciated that not all the discovered patterns exhibit such clear cut functional specificity. Several of them correspond to regions (e.g., loops, coiled-coils, transmembrane) which are traditionally considered uninteresting at least for the purposes of functionally annotating a protein. Sometimes, though, even such weak similarities can provide useful hints for the characterization of protein regions. We have implemented two mechanisms that allow the exploitation of this potential. First, the user is provided with the list of all the patterns which are matched by the query sequence. An expert user will, in most cases, be able to identify which patterns are of biological importance. Selection of a particular pattern leads then to a refinement of the scoring, focusing only on the areas of the database covered by this pattern. Second, when the underlying data base includes annotations of the various database sequence regions, this annotation is used in conjunction with the patterns for the extraction of useful information. Examples of the use of these two mechanisms are given in the next subsection.

B. Searching

In order to illustrate the searching phase (and to explain how it may be used), we selected two query sequences. The first is a well studied and annotated core histone 3 protein (SwissProt ID: H31_HUMAN), while the second is a not yet characterized ORF (SwissProt ID: YZ28_METJA) from *Methanococcus Jannaschii*.

H31_HUMAN

Core histones have been the object of extensive study due to their central role in the packaging of DNA within the cell. These small proteins are rich in positively charged amino-acids that help them bind to the negatively charged DNA double helix, see J. D. Watson, N. H. Hopkins, J. W. Roberts, J. Steitz and A. M. Weiner, "Molecular Biology of the Gene," The Benjamin/Cummings Publishing Company, Fourth Edition, 1987. The four core histones (H2A, H2B, H3 and H4) bind together into an octameric construct (reminiscent of a cylindrical wedge) that provides the substrate for 146 bps long DNA segments to wrap around, thus creating the nucleosome complexes within the cell chromatin.

The SwissProt Rel. 34 database contains 33 sequences which are annotated as Histones 3, among which is H31_HUMAN, the core histone 3 protein found in humans. The top-scoring results of searching this sequence with our homology detection tool are tabulated in FIG. 21. Next to each sequence is given the similarity score of the highest scoring local alignment between that sequence and H31_HUMAN. The scores mentioned in FIG. 21 are obtained using the PAM 130 matrix (see M. O. Dayhoff, R. M. Schwartz and B. C. Orcutt, "A model of evolutionary change in proteins," Atlas of Protein Sequence and Structure, 5:345–352, 1978) and every matching sequence from the database is assigned the score of its highest scoring segment.

All the 33 core Histones 3 of SwissProt Rel. 34 are correctly identified as homologous to H31_HUMAN. Furthermore, several other proteins (YB21_CAEEL, CENA_HUMAN, CSE4_YEAST, YL82_CAEEL, CENA_BOVIN, YMH3_CAEEL) are found to have extensive local similarities with H31_HUMAN. Inspection of the annotation for these proteins indicates that they are known histone 3-like proteins. As a final note, H3_NARPS (a known histone 3) appears within the release 34 of SwissProt only as a fragment and that is the reason that it is scored lowest in the list of results.

FIG. 22 gives a selected view (both high and low-scoring) of the alignments generated for the query sequence H31_HUMAN. In FIG. 22, local alignments of H31_HUMAN with a highly similar (H3_YEAST) and a moderately similar (CENA_HUMAN)protein are shown. For every sequence, a number of local similarities are reported. In every such similarity, the relevant query ("Query") and the data base sequence ("Seq") regions are listed one under the other having between them the resulting consensus regions. We use the character '+' to indicate chemically similar amino acids.

YZ28_METJA

H31_HUMAN is in a sense an easy test case because the database contains several sequences which are highly homologous to it. An interesting question to ask is how does our methodology fare when presented with "borderline" sequences, i.e., sequences for which no known homology exists. In an effort to address this question, the system was presented with the yet not annotated sequence YZ28_METJA, an open reading frame with 1272 residues from the genome of *M. jannaschii*.

The top scoring alignments produced by our system when presented with the query sequence YZ28_METJA are depicted in FIG. 23. The mutation matrix used is PAM130.

For the purposes of functional annotation of YZ28_METJA, the above mentioned results are not very enlightening as the database hits involve quite diverse proteins: the first two (NTNO_HUMAN, NTNO_BOVIN) are sodium-dependent noradrenaline transporters, while the last one (KAPL_APLCA) is a kinase.

With these questions in mind, we proceeded to a closer examination of the similarities between YZ28_METJA and the database sequences. For this analysis, every pattern matching YZ28_METJA was scrutinized individually. It is to be appreciated that the search phase of the invention allows the user to select any of the patterns matched by the query sequence at hand and focus on the local alignments induced by that particular pattern alone, disregarding all the other patterns. This feature was employed for each of the patterns matched by YZ28_METJA. The intention was to discover if any such pattern is specific to one particular protein family, thus giving clues about the functionality of YZ28_METJA.

Figure 28:
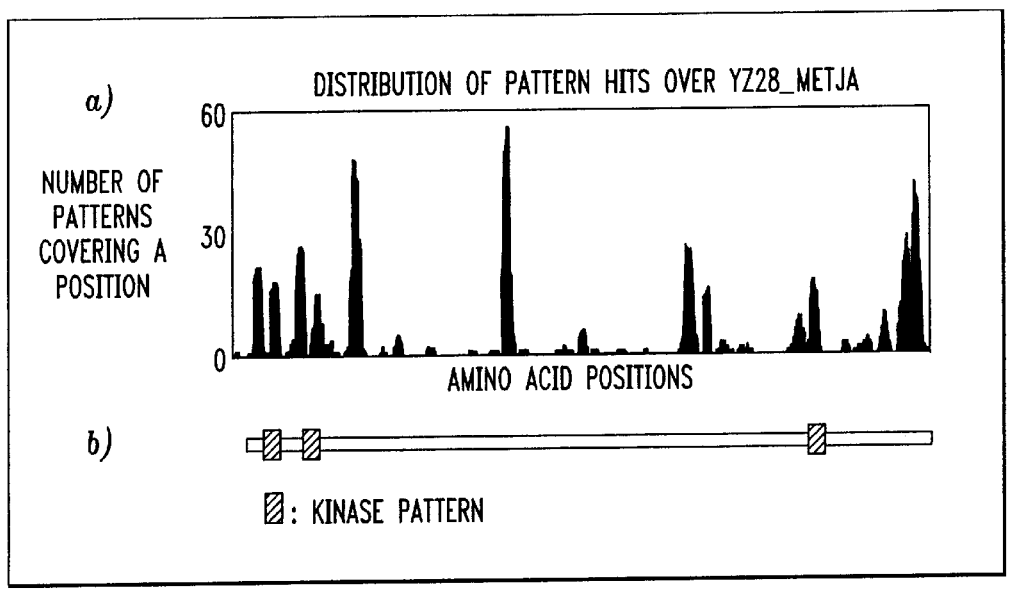

As it turned out, there exist three patterns (namely, the patterns "Y . . . S . . . L . . . DLK", "NIL . . . IKL" and "I.H.DLK . . . D") which are very specific for the kinase family. FIG. 24 describes a few among the top scoring alignments produced for the first one of them, that is, the top scoring local alignments for the query sequence YZ28_METJA induced by the pattern "Y . . . S . . . I . . . DLK". The mutation matrix used is PAM130. FIG. 25 contains a complete listing of all the database sequences containing that particular pattern. FIGS. 26 and 27 give the corresponding listings for the remaining two patterns. FIG. 28 provides a graphic representation of: (a) the distribution of all the patterns matched by YZ28_METJA and (b) the areas covered by the three kinase-specific patterns.

The pattern "Y . . . S . . . I . . . DLK" generates 24 hits within SwissProt. All of these proteins (with the exception of NABA_RAT, a sodium/bile acid cotransporter) are annotated as protein kinases (two of them, KD82_SCHPO and KKK1_YEAST, are characterized as putative/probable kinases) with the majority belonging or showing similarity to the serine/threonine kinase family. Furthermore, "Y . . . S . . . L . . . DLK" not only belongs to the kinase domain of these proteins but it actually contains the active site (amino acid D) of that domain.

In FIG. 25, SwissProt Rel. 34 sequences containing the pattern "Y . . . S . . . L . . . DLK" are shown. All of them are annotated as protein kinases or probable/putative protein kinases (almost exclusively of the serine/threonine variety). The only exception is the protein NABA_Rat which is annotated as a sodium/bile acid cotransporter.

Similar results are obtained for "NIL . . . IKL", the second of the three patterns, are shown in FIG. 26. In this case the number of database hits is 34 and all of them (excluding two unannotated ORFs from Yeast and Mycoplasma Hominis) are known (or probable) protein kinases. Again, serine/threonine kinases are the majority.

Finally, the third pattern "I.H.DLK . . . D" generates 30 SwissProt Rel. 34 hits, all of them known or putative protein kinases. This is shown in FIG. 27. Furthermore, as in the case of the first of the three patterns, the pattern "I.H.DLK . . . D" includes the active site of the kinase domain.

It is interesting to notice that all three of the aforementioned patterns are specific instances of (parts of) the following general pattern:

[LIVMFYC]. [HY].D[LIVMFY]K . . . N[LWMFYCT] [LIVMFYCT][LIVMFYCT]

where the notation [XYZ] indicates a position which can be occupied by any of the residues X, Y, Z. This more general pattern is the PROSITE database entry with accession number PS00108, namely, the signature of the serine/threonine protein kinase active site. Notice that this PROSITE signature is too specific for picking up a kinase catalytic site in the areas of YZ28_METJA covered by the three patterns examined above. This situation (known in the language of artificial intelligence as overrepresentation of the training set) is typical of learning systems trained by a finite subset of the entire universe: there is always the danger that the set of positive examples (in this case, the specific set of known serine/threonine kinases used by PROSITE) is biased and as a result the features learned (here the kinase signature) while explaining the observations are not general enough to extrapolate efficiently to new instances of the family under consideration (i.e., there are false negatives). The cure for this problem is the use of as large a training set as possible and this is the crux of the approach we present here.

As mentioned, FIG. 28 provides a graphic representation of: (a) the distribution of all the patterns matched by YZ28_METJA and (b) the areas covered by the three kinase-specific patterns.

In FIG. 28(a), there are 410 patterns (among those discovered in the information gathering phase) matched by YZ28_METJA. A pattern "covers" a residue position if it starts before (or at) that position and ends after (or at) that position. The chart shows, for each residue position (x-axis), how many patterns (y-axis) cover that position. As shown in FIG. 28(b), the three kinase pattern discussed in the text match the sequence at offsets 35 (pattern "Y . . . S . . . I . . . DLK"), 112 (pattern "NIL . . . IKL") and 1052 (pattern "I.H.DLK . . . D"). These offsets are depicted here relative to the spikes of the pattern distribution in FIG. 28(a).

Using Existing Annotation

Of the 410 patterns matched by YZ28_METJA, only the three patterns analyzed above exhibit such clear cut functional specificity. This does not mean that the remaining 407 are useless. The kind of biological inference that can be drawn from a local similarity between two sequences is not always of a functional nature. Sometimes the homology indicates preservation of structure and yet other times it might correspond to functional units of a supporting role (e.g., DNA-binding domains) in the overall function of the sequences compared. In an effort to explore such weaker similarities, we have provided for a way to exploit the annotation available in the underlying database. In the description given below we assume the SwissProt annotation format.

The SwissProt data base associates with most of its sequences annotations of sequence regions (the FT lines, see A. Bairoch and R. Apweiler, "The SWISS-PROT protein sequence data bank and its supplement TrEMBL in 1998", Nucleic Acids Res., 26:38–42, 1998). A typical region description looks like:

FT=DOMAIN 528 779 PROTEIN KINASE where the keyword "FT" indicates that this is a region description line and the remaining line describes the region by giving its starting and ending positions (from residue 528 up to and including residue 779 of the relevant data base sequence) and its annotation (a protein kinase domain).

When presented with a pattern P, we can use (as already mentioned) the offset list $L_D(P)$ to locate all the sequences in the database that match P. Assume that S is such a sequence and that at offset j within S begins a substring that matches P. If P happens to fall in an annotated region of S (either entirely or in part), we can associate this region with P. Performing this process for every sequence S matching P results in a set $RS_D(P)$ of regions associated with P. FIG. 29 gives an example of part of the output produced by our system for one of the three kinase patterns described above. That is, FIG. 29 illustrates analysis of individual patterns using the SwissProt annotation: some of the database sequences matching the pattern "AI H.DLK . . . D". For every such sequence, its ID and DE lines are reported (see A. Bairoch and R. Apweiler, "The SWISS-PROT protein sequence data bank and its supplement TrEMBL in 1998", Nucleic Acids Res., 26:38–42, 1998), giving the SwissProt name of the sequence and a short description of its functionality. Next follows the offset within the sequence where the match originates. Finally, there are the FT lines for all the annotated regions having an intersection with the region covered by the pattern.

Given now a pattern P matched by a subsequence A of a query sequence Q, the question is how to use $RS_D(P)$ in an effort to characterize A. A number of approaches can be used. For example, if $RS_D(P)$ is large enough and the majority of its members agree in their functionality, then it can be inferred that A is quite likely to have the same functionality. Another consideration is the relative lengths of the pattern P and the regions described by the FT lines. If, for example, a pattern P has an extent of 15 residues while an annotated sequence region containing P has a length of 300 amino acids then one might not want to transfer the annotation of that region to P. In conclusion, the end user is expected to apply his/her expertise in deciding how to best exploit the information provided by the system.

Figure 30:
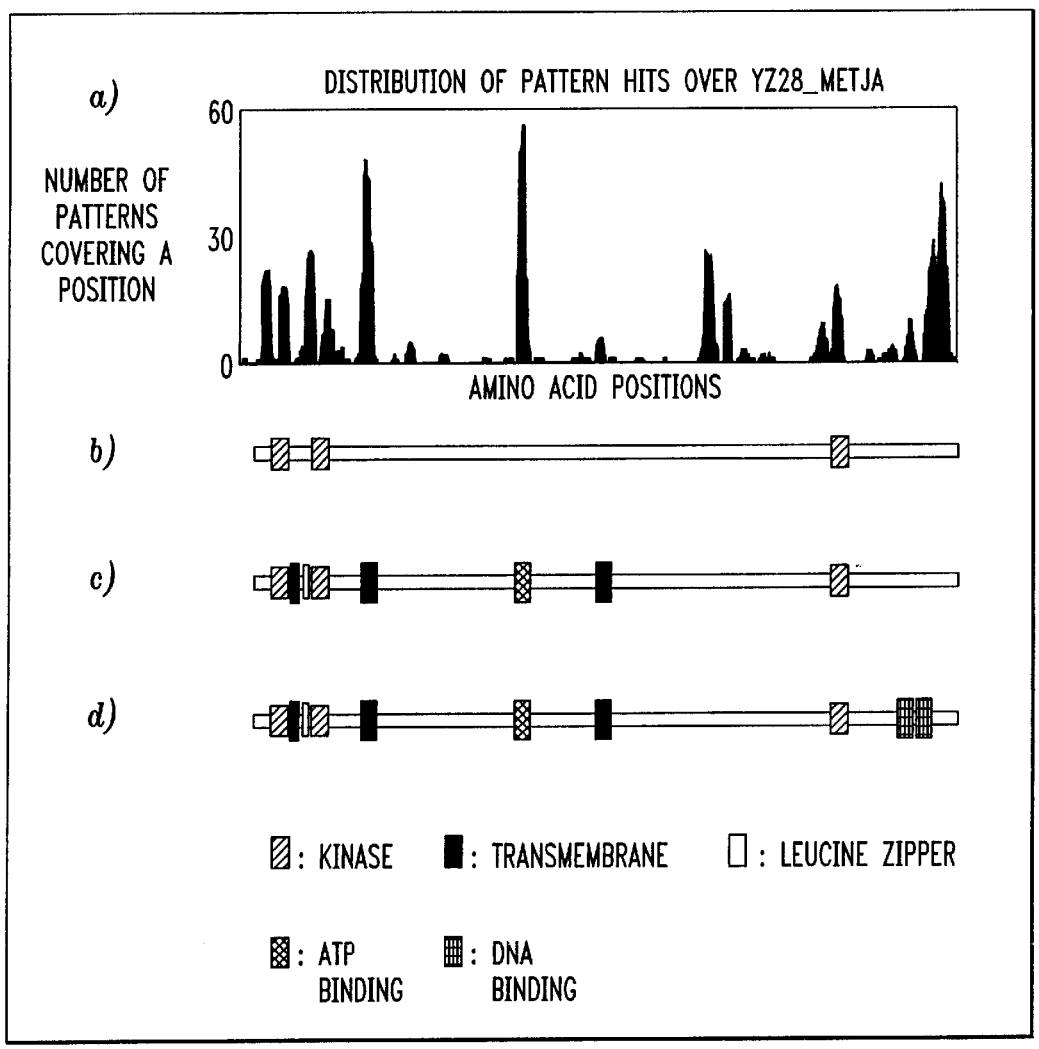

FIG. 30 illustrates two ways to use the sets $RS_D(P)$ for annotating regions of YZ28_METJA, thus extending the picture drawn in FIG. 28(b). That is, FIG. 30 shows a characterization of various segments of YZ28_METJA from the annotation of the patterns matched by these segments. The annotation of the patterns is obtained by exploiting the information available for the various regions of the database sequences also matching these patterns. The segments are shown again relative to the spikes of the distribution of patterns over the entire YZ28_METJA. The first approach (FIG. 30(b)) assigns an annotation X (e.g., X=transmembrane region) to a pattern P if: (i) the size of $RS_D(P)$ is at least 15; (ii) the majority (80%) of the regions in $RS_D(P)$ are annotated as X; and (iii) at least 50% of every region of $RS_D(P)$ annotated as X is covered by P. The second approach (FIG. 30(c)) shares the requirements (i) and (ii) above and relaxes (iii) by allowing the percentage of the annotated region covered by the pattern to be 30% or more.

Performance

The running time of a homology search for a query sequence Q depends on: (i) the size of the set of patterns Π used; and (ii) the actual number of local similarities (induced by the patterns matching Q) between Q and the database sequences. For the case of SwissProt Rel. 34 used here, typical searches for query proteins of size around a thousand residues take 4–6 seconds on a Pentium 266 MHz computer with 256 MB of memory. It should be mentioned that the running time reported above is achieved by keeping all the program data.(patterns and their offset lists) in memory. For SwissProt, this data occupies around 200 MB.

In accordance with the various aspects of the invention, we have provided a methodology for performing sequence similarity searches based on the discovery of patterns over an underlying database D of proteins and the use of these patterns for the identification of homologies between a query sequence and the proteins of the database at hand. We described a way to precisely define a set of patterns to be searched using statistical arguments and discussed how patterns provide more sensitivity in identifying significant homologies by introducing memory into the statistical computations. Finally, the utility of the methodology was exhibited using the SwissProt Rel. 34 database as a test bed and showing how the system can be used for annotating query sequences. In this context, we also discussed the potential of exploiting the discovered patterns in conjunction with the annotation of the underlying database towards characterizing even weak similarities between the query and the data base sequences.

Advantageously, one aspect of the sequence homology detection system of the invention that sets it apart from prior art pattern based tools for homology detection (e.g., BLOCKS) is the completeness of the set of patterns used. The patterns are learned in an unsupervised way from a very large training set, that of all the proteins within the underlying database D. There are no bias-creating prior assumptions on which sequences "should" be considered as members of the same family. As a result, the patterns discovered are expected to be more sensitive. Furthermore, by considering together sequences of distinct functionalities, we are able to discover weak similarities that span family boundaries (e.g., patterns that describe transmembrane regions). Such similarities, although not sufficient for the inference of functional annotations, nevertheless give useful information regarding the role of different parts of the query sequence under examination.

Another advantage of the system of the invention is the running times achieved for the homology searches. The speedup afforded by using patterns rather than scanning the entire database for every search can become a factor as the size of genomic databases increases ever faster (especially for users who want to run in-house tests rather than use public servers).

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A computer-based method of processing a plurality of sequences in a database, the method comprising the steps of:

evaluating each of the plurality of sequences including characters which form each sequence; and generating at least one pattern of characters representing at least a subset of the sequences in the database, the pattern having a statistical significance associated therewith, the statistical significance of the pattern being determined by a value representing a minimum number of sequences that the pattern supports in the database.

2. The method of claim 1, further comprising the step of collecting the generated patterns having the minimum support value into a set for use in comparison with a query sequence to detect one or more homologies between the query sequence and one or more sequences in the database.

3. The method of claim 1, wherein the statistical significance of a pattern further depends on at least one of a length parameter and a width parameter associated with the pattern.

4. The method of claim 1, wherein the minimum support value, represented as $K_{min}$, is calculated to be the first number K for which an inequality represented as:

$$\max_B \{Pr[X_{B,K} \geq N_{B,K}]\} \leq threshold$$

is satisfied, wherein $N_{B,K}$ represents a number of patterns with a backbone structure B which has support K within the database D, $X_{B,K}$ represents a random variable defined over i processed versions of D, i=1, ..., N, and threshold represents a predefined probability value.

5. The method of claim 4, wherein a pattern is represented by the expression:

$$\Sigma(\Sigma \cup \{`.`\})^*\Sigma$$

where $\Sigma$ represents an alphabet of permitted characters, and `.` represents a don't care character which relates to a position in the pattern that can be occupied by an arbitrary character in the alphabet $\Sigma$.

6. The method of claim 5, wherein the backbone structure B of a pattern is a string over a numerical value set $\{1, 0\}$ obtained when replacing characters of the pattern with a value of `1` and the don't care characters of the pattern by a value of `0.`

7. The method of claim 4, further comprising the step of generating each of the processed versions of D associated with the random variable $X_{B,K}$ by computing a random permutation of the characters in each sequence of D.

8. The method of claim 7, further comprising the step of computing a mean $s_{B,K}$ and a variance $m_{B,K}$ of the random variable $X_{B,K}$.

9. The method of claim 8, further comprising the step of computing a constant value C as a function of $N_{B,K}$ and the mean $s_{B,K}$ and the variance $m_{B,K}$ of the random variable $X_{B,K}$.

10. The method of claim 9, further comprising the step of computing an upper bound $p_{B,K}$ for the probability expression $Pr[X_{B,K} > N_{B,K}]$ as the inverse of the square of the constant value C.

11. The method of claim 10, wherein the minimum support value is the smallest number K wherein $\max_B \{p_{B,K}\} <$ threshold.

12. The method of claim 4, wherein threshold is selected to represent a confidence level associated with the minimum support value resulting from the inequality.

13. The method of claim 4, wherein the magnitude of threshold is inversely related to the magnitude of the minimum support value.

14. The method of claim 4, wherein the statistical significance of a pattern is directly related to the magnitude of the minimum support value.

15. The method of claim 1, further comprising the step of grouping two or more similar sequences in the database into a group prior to the evaluating step.

16. The method of claim 15, wherein two or more sequences are similar when, after alignment, a first sequence has at least a given percentage of characters in common with a second sequence.

17. The method of claim 16, wherein the longest sequence from the group is used in the evaluating step.

18. The method of claim 1, wherein the database includes sequences having both known and unknown sequence features.

19. The method of claim 1, wherein the sequences represent proteins.

20. Apparatus for processing a plurality of sequences in a database, the apparatus comprising:

at least one processor operative to: (i) evaluate each of the plurality of sequences including characters which form each sequence; and (ii) generate at least one pattern of characters representing at least a subset of the sequences in the database, the pattern having a statistical significance associated therewith, the statistical significance of the pattern being determined by a value representing a minimum number of sequences that the pattern supports in the database.

21. An article of manufacture for processing a plurality of sequences in a database, comprising a machine readable medium containing one or more programs which when executed implement the steps of:

evaluating each of the plurality of sequences including characters which form each sequence; and generating at least one pattern of characters representing at least a subset of the sequences in the database, the pattern having a statistical significance associated therewith, the statistical significance of the pattern being determined by a value representing a minimum number of sequences that the pattern supports in the database.

* * * * *